United States Patent [19]
Organ et al.

[11] Patent Number: 5,880,280
[45] Date of Patent: Mar. 9, 1999

[54] ARYL, ALKYL, ALKENYL AND ALKYNYLMACROLIDES HAVING IMMUNOSUPPRESSIVE ACTIVITY

[75] Inventors: Helen M. Organ, Fanwood; Mark A. Holmes, Edison, both of N.J.

[73] Assignee: Merck & Co., Inc., Rahway, N.J.

[21] Appl. No.: 259,831

[22] Filed: Jun. 15, 1994

[51] Int. Cl.$^6$ .................. C07D 267/22; C07D 281/18; C07D 337/16; C07D 513/00
[52] U.S. Cl. .................................................. 540/456
[58] Field of Search ................... 540/456, 291, 540/411

[56] References Cited

U.S. PATENT DOCUMENTS

| | | | |
|---|---|---|---|
| 3,244,592 | 4/1966 | Arai | 167/65 |
| 4,894,366 | 1/1990 | Okuhara et al. | 514/63 |
| 5,143,918 | 9/1992 | Bochis et al. | 514/291 |
| 5,162,334 | 11/1992 | Goulet et al. | 514/291 |
| 5,189,042 | 2/1993 | Goulet et al. | 514/291 |
| 5,190,950 | 3/1993 | Beattie et al. | 514/291 |
| 5,208,241 | 5/1993 | Ok et al. | 514/291 |
| 5,247,076 | 9/1993 | Goulet al. | 540/456 |
| 5,250,678 | 10/1993 | Goulet et al. | 540/456 |
| 5,252,732 | 10/1993 | Sinclair et al. | 540/456 |
| 5,262,533 | 11/1993 | Sinclair et al. | 540/456 |

FOREIGN PATENT DOCUMENTS

| | | | |
|---|---|---|---|
| 0 427 680 A1 | 5/1991 | European Pat. Off. | 540/456 |
| 2 244 991 A | 12/1991 | United Kingdom | 540/456 |
| 2 245 891 A | 1/1992 | United Kingdom | 540/456 |
| WO 89/05304 | 6/1989 | WIPO | 540/456 |
| WO 91/13889 | 9/1991 | WIPO | 540/456 |
| WO 92/00313 | 1/1992 | WIPO | 540/456 |
| WO 93/04679 | 3/1993 | WIPO | 540/456 |
| WO 93/04680 | 3/1993 | WIPO | 540/456 |

OTHER PUBLICATIONS

*Phase III Drug Profiles,* 3(7): 15–31 (Sep. 1993), "Tacrolimus".

Thompson, et al., *Springer Semin Immunopathol,* 14: 323–344 (1993). "FK 506: A Novel Immunosuppressant for treatment of autoimmune disease".

Organ, et al., *Abstract & Program Book—24th Nat'l Med. Chem. Symp.,* p. 99 (Jun. 21–25, 1994), "Novel Derivatives Based Upon Modifications of the Cyclohexyl Ring of L–683,590 . . . ".

Primary Examiner—John M. Ford
Assistant Examiner—Bruck Kifle
Attorney, Agent, or Firm—Mollie M. Yang; David L. Rose

[57] ABSTRACT

Aryl, alkyl, alkenyl and alkynyl macrolides of the general structural Formula I:

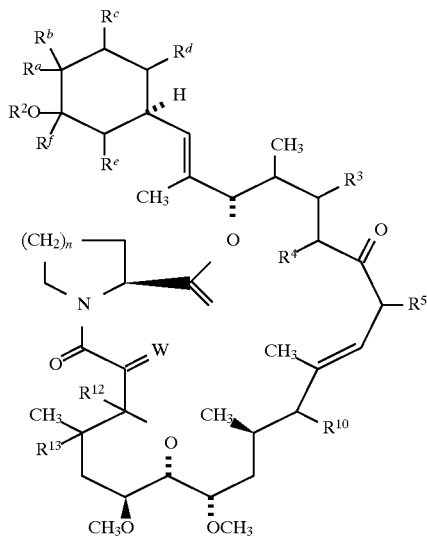

have been prepared from suitable precursors by modification at C-30, C-33, and/or C-34 of the cyclohexyl ring. These macrolide immunosuppressants are useful in a mammalian host for the treatment of autoimmune diseases, infectious diseases and/or the prevention of rejection of foreign organ transplants and/or related afflictions, diseases and illnesses.

1 Claim, No Drawings

ARYL, ALKYL, ALKENYL AND ALKYNYLMACROLIDES HAVING IMMUNOSUPPRESSIVE ACTIVITY

SUMMARY OF THE INVENTION

The present invention is related to aryl, alkyl, alkenyl and alkynylmacrolides which are useful in a mammalian subject for the treatment of autoimmune diseases (such as juvenile-onset or recent-onset diabetes mellitus, multiple sclerosis, and rheumatoid arthritis, liver disease, posterior uveitis, allergic encephalomyelitis, and glomerulonephritis), immunodepression, infectious diseases and/or the prevention of rejection of foreign organ transplants, (e.g. bone marrow, kidney, liver, heart, skin, small-bowel, and pancreatic islet-cell transplants, including xeno transplants), the topical treatment of inflammatory and hyperproliferative skin diseases and cutaneous manifestations of immunologically-mediated illnesses (such as: psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus or Alopecia areata), male pattern alopecia, alopecia senilis, reversible obstructive airways disease, particularly asthma, inflammation of mucosa and blood vessels, cytomegalovirus infection, multidrug resistance, idiopathic thromboytopenic purpura, Behcet's syndrome, conjunctivitis, Crohn's disease, Mooren's ulcer, uveitis, servere intraocular inflammation and/or hepatic injury associated with ischemia. The present compounds are further useful in combination with a 5α-reductase inhibitor, a cyclosporin, a potassium channel opener or a phospholipid in a mammalian host for the treatment of baldness, especially male pattern alopecia, female pattern alopecia, alopecia senilis, or alopecia areata. In addition, some of the compounds of this invention may have antagonistic properties and so have utility in the reversal of immunosuppressive activity and/or diminishing the toxicity of other immunosuppressive agents.

More particularly, this invention relates to compounds of the general structural Formula I:

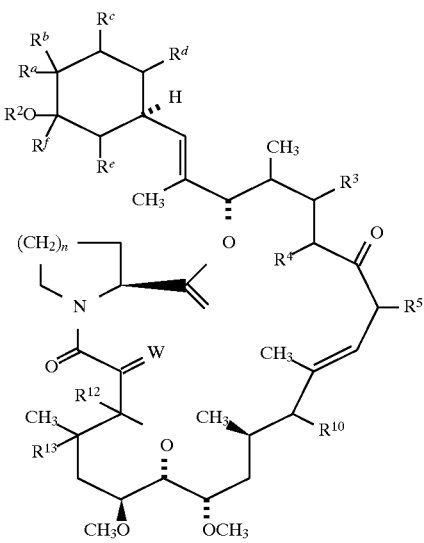

wherein $R^a$, $R^b$, $R^c$, $R^d$, $R^e$, $R^f$, $R^2$, $R^3$, $R^4$, $R^5$, $R^{10}$, $R^{12}$, $R^{13}$, W and n are hereinafter defined.

This invention also relates to pharmaceutical compositions containing the compounds and to a method of use of the present compounds and other agents for the treatment of and prevention of certain afflictions, diseases and illnesses.

BRIEF DESCRIPTION OF DISCLOSURES IN THE ART

Fujisawa United States, European and Japanese patents and applications (U.S. Pat. No. 4,894,366, issued Jan. 16, 1990, EPO Publication No. 0,184,162 and PBJ Disclosure 63-17884) and publications (J. Am. Chem. Soc., 1987, 109, 5031 and J. Antibiotics 1987, 40, 1249) disclose 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (FR-900506) (FK-506) (L-679,934), 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,}$ $_9$]-octacos-18-ene-2,3,10,16-tetraone (FR-900520) and related compounds which are the starting materials for the preparation of the compounds described. The synthetic preparation of the aforementioned starting material (FR-900506) has been reported (J. Am. Chem. Soc., 1989, 111, 1157). A Sandoz U.S. patent (U.S. Pat. No. 5,011,844) and European patent application (EPO Publication No. 0,356,399) disclose stereoisomers of FR-900506 and derivatives at the 17-position. Fisons European and WIPO patent applications (EPO Publication No. 0,323,042 and PCT Publication No. WO89/05304) disclose various derivatives of FR-900506, FR-900520 and related compounds. A Sandoz European patent application (EPO Publication No. 0,437,680) discloses chloro, bromo, iodo and azido derivatives of FR-900506, FR-900520 and related compounds. An Abbott patent application (PCT Publication No. WO 93/04680) discloses certain C-32 and C-33 derivatives of FR-900506, FR-900520 and related compounds. A Merck European patent application (EPO Publication No. 0,428,365) discloses various amino derivatives of FR-900506, FR-900520 and related compounds. A Fujisawa UK patent application (UK Publication No. GB 2,245,891A) discloses various aryl(lower alkyl) and heteroaryl derivatives of FR-900506, FR-900520 and related compounds. Merck U.S. Pat. Nos. 5,247,076, 5,250,678 and 5,252,732 disclose various aryl and heteroaryl derivatives of FR-900506, FR-900520 and related compounds. Merck U.S. Pat. No. 5,284,877 discloses C-17 alkyl and alkenyl derivatives of FR-900506, FR-900520 and related compounds.

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, type 2 adult onset diabetes, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was approved by the U.S. FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, tacrolimus, FR-900506, FK-506,

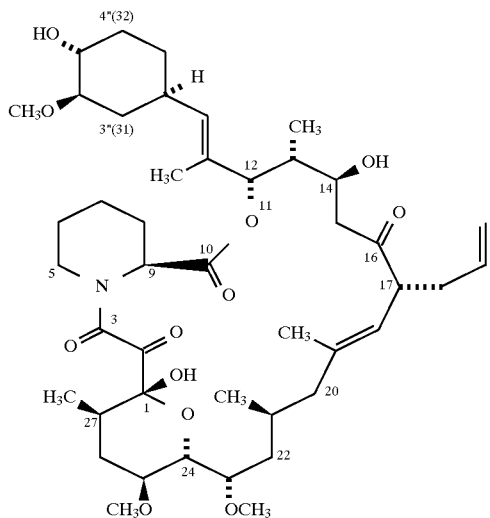

(17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$] octacos-18-ene-2,3,10,16-tetraone) and related compounds which were isolated and characterized by Tanaka, Kuroda, and co-workers at Fujisawa Pharmaceutical Co. in Japan, see *J. Am. Chem. Soc.,* 1987, 109, 5031, and U.S. Pat. No. 4,894,366, issued Jan. 16, 1990) have been shown to possess exceptional immunosuppressive activity. Fujisawa United States patents (U.S. Pat. No. 4,929,611, issued May 29, 1990 and U.S. Pat. No. 4,956,352, issued Sep. 11, 1990) disclose the use of FK-506-type compounds in treating resistance to transplantation. In particular, the compound FR-900506 has been reported to be 100 times more effective than cyclosporin in the supression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), male pattern alopecia or alopecia senilis (EPO Publication No. 0,423,714), rheumatoid arthitis (C. Arita, et al., *Clinical Exp. Immunol.,* 1990, 82, 456–461; N. Inamura, et al., *Clin. Immunol. Immunopathol.* 1988, 46, 82–90), recent-onset diabetes (N. Murase, et al., *Diabetes,* 1990, 39, 1584–86; N. Murase, et al., *Lancet,* 1990, 336, 373–74), posterior uveitis (H. Kawashima, *Invest. Ophthalmol. Vis. Sci.,* 1988, 29, 1265–71), hepatic injury associated with ischemia (M. Sakr, et al., *Life Sci.,* 1990, 47, 687–91), allergic encephalomyelitis (K. Deguchi, et al., *Brain Nerve,* 1990, 42, 391–97), glomerulonephritis (J. McCauley, et al., *Lancet,* 1990, 335, 674), systemic lupus erythematosus (K. Takabayashi, et al., *Clin. Immunol. Immunopathol.,* 1989, 51, 110–117), multidrug resistance (M. Naito, et al., *Cancer Chemother. Pharmacol.,* 1992, 29, 195–200), inflammation of mucosa and blood vessels (PCT Publication WO 92/17754), cytomegalovirus infection (UK Publication GB 2,247,620A), and idiopathic thrombocytopenic purpura and Basedow's disease (PCT Publication WO 91/19495).

DETAILED DESCRIPTION OF THE INVENTION

A. Scope of the Invention

The novel compound of this invention has structural Formula I:

or a pharmaceutically acceptable salt thereof, wherein:
$R^a$ is selected from the group consisting of:
(1) hydrogen,
(2) hydroxy,
(3) $C_{1-6}$alkoxy,
(4) aryl-$C_{1-6}$alkoxy-,
(5) substituted aryl-$C_{1-3}$alkoxy-, in which the substituents on aryl are X, Y and Z,
(6) unsubstituted or substituted aryloxy, in which the substituents on aryl are X, Y and Z,
(7) heteroaryl-$C_{1-3}$alkoxy-,
(8) substituted heteroaryl-$C_{1-3}$alkoxy-, in which the substituents on heteroaryl are X, Y and Z,
(9) unsubstituted or substituted heteroaryloxy, in which the substituents on heteroaryl are X, Y and Z,
(10) —OCO—$C_{1-6}$alkyl,

(11) —OCONR$^6$R$^7$, and
(12) —OR$^{11}$;
R$^b$ is selected from:
(1) hydrogen, and
(2) hydroxy,
or R$^a$ and R$^b$ taken together form the group oxo;
R$^c$, R$^d$, and R$^e$ are independently:
(1) —A—R$^1$, wherein R$^1$ is as defined below and A is independently selected from:
  (a) —O—,
  (b) —S—, and
  (c) —NR$^6$—, wherein R$^6$ is as defined below; or
(2) hydrogen, with the provisio that at least one of R$^c$, R$^d$, and R$^e$ are other than hydrogen,
or R$^c$ with its adjacent hydrogen atom may form the group oxo;
R$^f$ is hydrogen or R$^f$ and R$^e$ taken together form a double bond;
R$^1$ is selected from the group consisting of:
(1) C$_{1-10}$alkyl
(2) substituted C$_{1-10}$alkyl wherein the alkyl is substituted with one or more of the substituent(s) selected from:
  (a) aryl,
  (b) substituted aryl in which the substituents are X, Y and Z,
  (c) heteroaryl,
  (d) substituted heteroaryl in which the substituents are X, Y and Z,
  (e) C$_{1-6}$alkoxy,
  (f) aryloxy,
  (g) substituted aryloxy in which the substituents are X, Y and Z,
  (h) heteroaryloxy,
  (i) substituted heteroaryloxy in which the substituents are X, Y and Z,
  (j) aryl-C$_{1-3}$alkoxy,
  (k) substituted aryl-C$_{1-3}$alkoxy, in which the substituents on aryl are X, Y and Z,
  (l) hydroxy,
  (m) oxo,
  (n) —OCO—C$_{1-6}$alkyl
  (o) —NR$^6$R$^7$, wherein R$^6$ and R$^7$ are independently selected from:
    (i) hydrogen,
    (ii) C$_{1-10}$alkyl unsubstituted or substituted with one or more of the substituent(s) selected from:
      (a') aryl, which is unsubstituted or substituted with X, Y and Z,
      (b') heteroaryl, which is unsubstituted or substituted with X, Y and Z,
      (c') —OH,
      (d') C$_{1-6}$alkoxy,
      (e') —CO$_2$H,
      (f') —CO$_2$—C$_{1-6}$alkyl,
      (g') —C$_{3-7}$cycloalkyl, and
      (h') —OR$^{11}$,
    (iii) C$_{3-10}$alkenyl unsubstituted or substituted with one or more of the substituent(s) selected from:
      (a') aryl, which is unsubstituted or substituted with X, Y and Z,
      (b') heteroaryl, which is unsubstituted or substituted with X, Y and Z,
      (c') —OH,
      (d') C$_{1-6}$alkoxy,
      (e') —CO$_2$H,
      (f') —CO$_2$—C$_{1-6}$alkyl,
      (g') —C$_{3-7}$cycloalkyl, and
      (h') —OR$^{11}$,
    (iv) or where R$^6$ and R$^7$ and the N to which they are attached may form an unsubstituted or substituted 3–7-membered heterocyclic ring which may include one or two additional heteroatoms independently selected from the group consisting of O, S(O)$_p$, NR$^{14}$, wherein R$^{14}$ is hydrogen or C$_{1-6}$alkyl unsubstituted or substituted by phenyl, and p is 0, 1 or 2, such as morpholine, thiomorpholine, piperidine, or piperizine,
  (p) —NR$^6$CO—C$_{1-6}$alkyl-R$^7$,
  (q) —NR$^6$CO$_2$—C$_{1-6}$alkyl-R$^7$,
  (r) —NR$^6$CONR$^6$R$^7$,
  (s) —OCONR$^6$R$^7$,
  (t) —COOR$^6$,
  (u) —CHO,
  (v) —OR$^{11}$, and
  (w) —S(O)$_p$—C$_{1-6}$alkyl;
(3) substituted or unsubstituted C$_{1-10}$alkyl wherein one or more of the alkyl carbons is replaced by a group selected from: —NR$^6$—, —O—, —S(O)$_p$—, —CO$_2$—, —O$_2$C—, —CONR$^6$—, —NR$^6$CO—, and —NR$^6$CONR$^7$—, and the alkyl may be substituted with one or more of the substituent(s) selected from:
  (a) aryl,
  (b) substituted aryl in which the substituents are X, Y and Z,
  (c) heteroaryl,
  (d) substituted heteroaryl in which the substituents are X, Y and Z,
  (e) C$_{1-6}$alkoxy,
  (f) aryloxy,
  (g) substituted aryloxy in which the substituents are X, Y and Z,
  (h) heteroaryloxy,
  (i) substituted heteroaryloxy in which the substituents are X, Y and Z,
  (j) aryl-C$_{1-3}$alkoxy,
  (k) substituted aryl-C$_{1-3}$alkoxy, in which the substituents on aryl are X, Y and Z,
  (l) hydroxy,
  (m) oxo,
  (n) —OCO—C$_{1-6}$alkyl,
  (o) —NR$^6$R$^7$, wherein R$^6$ and R$^7$ are defined above,
  (p) —NR$^6$CO—C$_{1-6}$alkyl-R$^7$,
  (q) —NR$^6$CO$_2$—C$_{1-6}$alkyl-R$^7$,
  (r) —NR$^6$CONR$^6$R$^7$,
  (s) —OCONR$^6$R$^7$,
  (t) —COOR$^6$,
  (u) —CHO,
  (v) —OR$^{11}$, and
  (w) —S(O)$_p$—C$_{1-6}$alkyl;
(4) C$_{1-10}$alkenyl wherein alkenyl contains one to four double bonds;
(5) substiuted C$_{1-10}$alkenyl wherein the alkenyl contains one to four double bonds and the alkyl or alkenyl may be substituted with one or more of the substituent(s) selected from:
  (a) aryl,
  (b) substituted aryl in which the substituents are X, Y and Z,
  (c) heteroaryl,
  (d) substituted heteroaryl in which the substituents are X, Y and Z,
  (e) C$_{1-6}$alkoxy,
  (f) aryloxy, (g) substituted aryloxy in which the substituents are X, Y and Z,
(h) heteroaryloxy,
(i) substituted heteroaryloxy in which the substituents are X, Y and Z,
(j) aryl-$C_{1-3}$alkoxy,
(k) substituted aryl-$C_{1-3}$alkoxy, in which the substituents on aryl are X, Y and Z,
(l) hydroxy,
(m) oxo,
(n) —OCO—$C_{1-6}$alkyl
(o) —$NR^6R^7$, wherein $R^6$ and $R^7$ are as defined above,
(p) —$NR^6CO$—$C_{1-6}$alkyl-$R^7$,
(q) —$NR^6CO_2$—$C_{1-6}$alkyl-$R^7$,
(r) —$NR^6CONR^6R^7$,
(s) —$OCONR^6R^7$,
(t) —$COOR^6$,
(u) —CHO,
(v) —$OR^{11}$, and
(w) —$S(O)_p$—$C_{1-6}$alkyl;

(6) $C_{2-10}$alkenyl wherein alkenyl contains one to four double bonds and wherein one or more of the alkyl carbons is replaced by a group selected from: —$NR^6$—, —O—, —$S(O)_p$—, —$CO_2$—, —$O_2C$—, —$CONR^6$—, —$NR^6CO$—, and —$NR^6CONR^7$—;

(7) substituted $C_{2-10}$alkenyl wherein alkenyl contains one to four double bonds and wherein one or more of the alkyl carbons may be replaced by a group selected from: —$NR^6$—, —O—, —$S(O)_p$—, —$CO_2$—, —$O_2C$—, —$CONR^6$—, —$NR^6CO$—, and —$NR^6CONR^7$, and the alkyl or alkenyl may be substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) aryloxy,
(g) substituted aryloxy in which the substituents are X, Y and Z,
(h) heteroaryloxy,
(i) substituted heteroaryloxy in which the substituents are X, Y and Z,
(j) aryl-$C_{1-3}$alkoxy,
(k) substituted aryl-$C_{1-3}$alkoxy, in which the substituents on aryl are X, Y and Z,
(l) hydroxy,
(m) oxo,
(n) —OCO—$C_{1-6}$alkyl,
(o) —$NR^6R^7$, wherein $R^6$ and $R^7$ are as defined above,
(p) —$NR^6CO$—$C_{1-6}$alkyl-$R^7$,
(q) —$NR^6CO_2$—$C_{1-6}$alkyl-$R^7$,
(r) —$NR^6CONR^6R^7$,
(s) —$OCONR^6R^7$,
(t) —$COOR^6$,
(u) —CHO,
(v) —$OR^{11}$, and
(w) —$S(O)_p$—$C_{1-6}$alkyl;

(8) $C_{2-10}$alkynyl wherein the alkynyl contains one to four double bonds;

(9) substituted $C_{2-10}$alkynyl wherein the alkynyl contains one to four double bonds and the alkyl or alkynyl may be substituted with one or more of the substituent(s) selected from:

(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) aryloxy,
(g) substituted aryloxy in which the substituents are X, Y and Z,
(h) heteroaryloxy,
(i) substituted heteroaryloxy in which the substituents are X, Y and Z,
(j) aryl-$C_{1-3}$alkoxy,
(k) substituted aryl-$C_{1-3}$alkoxy, in which the substituents on aryl are X, Y and Z,
(l) hydroxy,
(m) oxo,
(n) —OCO—$C_{1-6}$alkyl,
(o) —$NR^6R^7$, wherein $R^6$ and $R^7$ are as defined above,
(p) —$NR^6CO$—$C_{1-6}$alkyl-$R^7$,
(q) —$NR^6CO_2$—$C_{1-6}$alkyl-$R^7$,
(r) —$NR^6CONR^7$,
(s) —$OCONR^6R^7$,
(t) —$COOR^6$,
(u) —CHO,
(v) —$OR^{11}$, and
(w) —$S(O)_p$—$C_{1-6}$alkyl;

(10) $C_{2-10}$alkynyl wherein alkynyl contains one to four double bonds and wherein one or more of the alkyl carbons is replaced by a group selected from: —$NR^6$—, —O—, —$S(O)_p$—, —$CO_2$—, —$O_2C$—, —$CONR^6$—, —$NR^6CO$—, and —$NR^6CONR^7$-;

(11) substituted $C_{2-10}$alkynyl wherein alkynyl contains one to four double bonds and wherein one or more of the alkyl carbons may be replaced by a group selected from: —$NR^6$—, —O—, —$S(O)_p$—, —$CO_2$—, —$O_2C$—, —$CONR^6$—, —$NR^6CO$—, and —$NR^6CONR^7$, and the alkyl may be substituted with one or more of the substituent(s) selected from:
(a) aryl,
(b) substituted aryl in which the substituents are X, Y and Z,
(c) heteroaryl,
(d) substituted heteroaryl in which the substituents are X, Y and Z,
(e) $C_{1-6}$alkoxy,
(f) aryloxy,
(g) substituted aryloxy in which the substituents are X, Y and Z,
(h) heteroaryloxy,
(i) substituted heteroaryloxy in which the substituents are X, Y and Z,
(j) aryl-$C_{1-3}$alkoxy,
(k) substituted aryl-$C_{1-3}$alkoxy, in which the substituents on aryl are X, Y and Z,
(l) hydroxy,
(m) oxo,
(n) —OCO—$C_{1-6}$alkyl
(o) —$NR^6R^7$, wherein $R^6$ and $R^7$ are as defined above,
(p) —$NR^6CO$—$C_{1-6}$alkyl-$R^7$,
(q) —$NR^6CO_2$—$C_{1-6}$alkyl-$R^7$,
(r) —$NR^6CONR^6R^7$,
(s) —$OCONR^6R^7$,
(t) —$COOR^6$,
(u) —CHO, (v) —$OR^{11}$, and
(w) —$S(O)_p$—$C_{1-6}$alkyl;
(12) aryl
(13) heteroaryl;
(14) substituted aryl in which the substituents are X, Y and Z;
(15) substituted heteroaryl in which the substituents are X, Y and Z;
$R^2$ is selected from:
(1) hydrogen;
(2) $C_{1-10}$alkyl;
(3) substituted-$C_{1-10}$alkyl in which one or more substituent(s) is(are) selected from:
(a) hydroxy,
(b) oxo,
(c) $C_{1-6}$alkoxy,
(d) aryl-$C_{1-3}$alkoxy,
(e) substituted aryl-$C_{1-3}$alkoxy, in which the substituents on aryl are X, Y and Z,
(f) unsubstituted or substituted aryloxy, in which the substituents on aryl are X, Y and Z,
(g) —OCO—$C_{1-6}$alkyl,
(h) —$NR^6R^7$, wherein $R^6$ and $R^7$ are as defined above
(i) —$NR^6CO$—$C_{1-6}$alkyl-$R^7$, wherein $R^6$ and $R^7$ are as defined above,
(j) —$COOR^6$, wherein $R^6$ is as defined above,
(k) —CHO,
(l) —$OR^{11}$,
(m) —$S(O)_p$—$C_{1-6}$alkyl;
(4) $C_{3-10}$alkenyl;
(5) substituted $C_{3-10}$alkenyl in which one or more substituent(s) is(are) selected from:
(a) hydroxy,
(b) oxo,
(c) $C_{1-6}$alkoxy,
(d) aryl-$C_{1-3}$alkoxy,
(e) substituted aryl-$C_{1-3}$alkoxy, in which the substituents on aryl are X, Y and Z,
(f) unsubstituted or substituted aryloxy, in which the substituents on aryl are X, Y and Z,
(g) —OCO—$C_{1-6}$alkyl,
(h) —$NR^6R^7$, wherein $R^6$ and $R^7$ are as defined above
(i) —$NR^6CO$—$C_{1-6}$alkyl-$R^7$, wherein $R^6$ and $R^7$ are as defined above,
(j) —$COOR^6$, wherein $R^6$ is as defined above,
(k) —CHO,
(l) —$OR^{11}$,
(m) —$S(O)_p$—$C_{1-6}$alkyl;
(6) $C_{3-10}$alkynyl;
(7) substituted $C_{3-10}$alkynyl in which one or more substituent(s) is(are) selected from:
(a) hydroxy,
(b) oxo,
(c) $C_{1-6}$alkoxy,
(d) aryl-$C_{1-3}$alkoxy,
(e) substituted aryl-$C_{1-3}$alkoxy, in which the substituents on aryl are X, Y and Z,
(f) unsubstituted or substituted aryloxy, in which the substituents on aryl are X, Y and Z,
(g) —OCO—$C_{1-6}$alkyl,
(h) —$NR^6R^7$, wherein $R^6$ and $R^7$ are as defined above
(i) —$NR^6CO$—$C_{1-6}$alkyl-$R^7$, wherein $R^6$ and $R^7$ are as defined above,
(j) —$COOR^6$, wherein $R^6$ is as defined above,
(k) —CHO,
(l) —$OR^{11}$,
(m) —$S(O)_p$—$C_{1-6}$alkyl;
$R^3$ is hydrogen, hydroxy, —$OR^{11}$, or $C_{1-6}$alkoxy;
$R^4$ is hydrogen, or $R^3$ and $R^4$ taken together form a double bond;
$R^5$ is methyl, ethyl, propyl or allyl;
$R^{10}$ is hydrogen, hydroxy, —$OR^{11}$ or fluoro;
$R^{11}$ is selected from:
(a) —PO(OH)O—$M^+$, wherein $M^+$ is a positively charged inorganic or organic counterion,
(b) —$SO_3$—$M^+$,
(c) —$CO(CH_2)_qCO_2$—M+, wherein q is 1–3, and
(d) —CO—$C_{1-6}$alkyl-$NR^6R^7$, wherein $R^6$ and $R^7$ are as defined above and the alkyl is unsubstituted or substituted with one or more substituents selected from:
(i) hydroxy,
(ii) $C_{1-6}$alkoxy,
(iii) —$NR^{16}R^{17}$, wherein $R^{16}$ and $R^{17}$ are independently selected from:
(a') hydrogen, and
(b') $C_{1-6}$alkyl,
(vi) —$COOR^6$, wherein $R^6$ is as defined above,
(v) phenyl,
(iv) substituted phenyl in which the substituents are X, Y and Z,
(vii) heteroaryl,
(viii) —SH, and
(ix) —S—$C_{1-6}$alkyl;
$R^{12}$ is OH, H, or $R^{12}$ and $R^{13}$ taken together form a double bond;
W is O, (H, OH) or (H,H);
X, Y and Z independently are selected from:
(a) hydrogen,
(b) $C_{1-10}$alkyl, unsubstituted or substituted with one or more substituents selected from:
(i) aryl,
(ii) substituted aryl in which the substituents are X', Y' and Z',
(iii) heteroaryl,
(iv) substituted heteroaryl in which the substituents are X', Y', and Z',
(v) unsubstituted or substituted aryloxy, in which the substituents on aryl are X', Y' and Z',
(vi) —$OR^6$,
(vii) —$OR^{11}$,
(viii) —$OCOR^6$,
(ix) —$OCO_2R^6$,
(x) —$NR^6R^7$,
(xi) —CHO,
(xii) —$NR^6COC_{1-6}$alkyl-$R^7$,
(xiii) —$NR^6CO_2C_{1-6}$alkyl-$R^7$,
(xiv) —$NR^6CONR^6R^7$,
(xv) —$OCONR^6R^7$,
(xvi) —$CONR^6R^7$,
(c) $C_{1-10}$alkyl wherein one or more of the alkyl carbons is replaced by a group selected from —$NR^6$—, —O—, —$S(O)_p$—, —$CO_2$—, —$O_2C$—, —$CONR^6$—, —$NR^6CO$—, —$NR^6CONR^7$—, —CO—, —CH(OH)—, alkenyl or alkynyl and the alkyl may be unsubstituted or substituted with one or more substituents selected from:
(i) aryl,
(ii) substituted aryl in which the substituents are X', Y' and Z',
(iii) heteroaryl,
(iv) substituted heteroaryl in which the substituents are X', Y', and Z', (v) unsubstituted or substituted aryloxy, in which the substituents on aryl are X', Y', and Z',
(vi) —$OR^6$,
(vii) —$OR^{11}$,
(viii) —$OCOR^6$,
(ix) —$OCO_2R^6$,
(x) —$NR^6R^7$,
(xi) —CHO
(xii) —$NR^6COC_{1-6}alkyl-R^7$,
(xiii) —$NR^6CO_2C_{1-6}alkyl-R^7$,
(xiv) —$NR^6CONR^6R^7$,
(xv) —$OCONR^6R^7$,
(xvi) —$CONR^6R^7$, (d) aryl,
(e) substituted aryl wherein the substituents are X', Y' or Z',
(f) heteroaryl,
(g) substituted heteroaryl wherein the substituents are X', Y' or Z',
(h) substituted and unsubstituted aryloxy wherein the substitutents are X', Y', or Z',
(i) substituted and unsubstituted heteroaryloxy wherein the substitutents are X', Y', or Z',
(j) —$NO_2$,
(k) halogen,
(l) —$NR^6R^7$,
(m) —CN,
(n) —CHO,
(o) —$CF_3$,
(p) —$SR^8$, wherein $R^8$ is hydrogen, $C_{1-6}$alkyl, trifluoromethyl, or phenyl,
(q) —$SOR^8$,
(r) —$SO_2R^8$,
(s) —$CONR^6R^7$,
(t) $R^9O(CH_2)_m$— wherein $R^9$ is hydrogen, $C_{1-6}$alkyl, hydroxy-$C_{2-3}$alkyl, —$CF_3$, phenyl, $R^{11}$ or naphthyl and m is 0, 1, 2, or 3,
(u) —$CH(OR^{12})(OR^{13})$, wherein $R^{12}$ and $R^{13}$ are $C_{1-3}$ alkyl or taken together form an ethyl or propyl bridge,
(v) $R^9CO(CH_2)_m$— wherein $R^9$ and m are as defined above,
(w) $R^9O_2C(CH_2)_m$— wherein $R^9$ and m are as defined above, and
(x) —$R^{11}$; or any two of X, Y and Z may be joined to form a saturated ring having 5, 6 or 7 ring atoms, said ring atoms comprising 1 or 2 oxygen atoms, the remaining ring atoms being carbon, such as dioxolanyl or dioxanyl;

X', Y' and Z' independently are selected from:
(a) hydrogen,
(b) $C_{1-7}$alkyl,
(c) $C_{2-6}$alkenyl,
(d) halogen,
(e) —$NO_2$,
(f) —$NR^6R^7$, wherein $R^6$, and $R^7$ are as defined above,
(g) —CN,
(h) —CHO,
(i) —$CF_3$,
(j) —$SR^8$, wherein $R^8$ is hydrogen, $C_{1-6}$alkyl, trifluoromethyl, or phenyl,
(k) —$SOR^8$, wherein $R^8$ is as defined above,
(l) —$SO_2R^8$, wherein $R^8$ is as defined above,
(m) —$CONR^6R^7$, wherein $R^6$ and $R^7$ are as defined above,
(n) $R^9O(CH_2)_m$— wherein $R^9$ and m are as defined above,
(o) —$CH(OR^{12})(OR^{13})$, wherein $R^{12}$ and $R^{13}$ are as defined above,
(p) $R^9CO(CH2)_m$— wherein $R^9$ and m are as defined above,
(q) $R^9O_2C(CH_2)_m$— wherein $R^9$ and m are as defined above, and
(r) —$R^{11}$; and
n is 1 or 2.

The compounds of the present invention have asymmetric centers and this invention includes all of the optical isomers and mixtures thereof.

In addition compounds with carbon-carbon double bonds may occur in Z- and E-forms with all isomeric forms of the compounds being included in the present invention.

When any variable (e.g., alkyl, aryl, $R^6$, $R^7$, $R^8$, $R^9$, $R^{10}$, $R^{11}$, etc.) occurs more than one time in any variable or in Formula I, its definition on each occurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkanoyl" is intended to include those alkylcarbonyl groups of specified number of carbon atoms, which are exemplified by formyl, acetyl, propanoyl and butyryl; "alkanoyloxy" is intended to include those alkylcarbonyl groups of specified number of carbon atoms attached through an oxygen bridge, which are exemplified by formyloxy, acetoxy, propionoyloxy, and butyryloxy. "Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethyl pentenyl, and the like, and includes E and Z forms, where applicable; and "aryalkyl" represents aryl groups as herein defined which are attached through a straight or branched chain alkyl group of from one to six carbon atoms, such as, for example, benzyl, phenethyl, 3,3-diphenylpropyl, and the like. "Halogen", as used herein, means fluoro, chloro, bromo and iodo.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with amines of the formula $HNR^6R^7$).

The heteroaryl group as used herein includes acridine, carbazole, cinnoline, dibenzofuran, dibenzothiophene, quinoxaline, pyrrazole, indole, imidazole, benzimidazole, benzotriazole, furan, benzofuran, quinoline, isoquinoline, pyrazine, pyridazine, pyridine, pyrimidine, pyrrole which are optionally substituted.

In the compounds of Formula I the heteroaryl group may be optionally substituted with X, Y and Z at any available carbon atom or nitrogen atom (if present), but compounds bearing certain of X, Y and Z directly substituted to a nitrogen atom of the heteroaryl ring may be relatively unstable and are not preferred.

The aryl or aromatic group includes phenyl or naphthyl which are optionally substituted by from one- to three-members independently selected from the group consisting of: alkyl, alkenyl, halogen, carboxyl, CHO, amino, mono-alkylamino, di-alkylamino, aminoalkyl, mono-alkylaminoalkyl, di-alkylaminoalkyl, alkylthio, alkylsulfinyl, alkysulfonyl, trifluoromethyl, amido, mono-alkylamido, dialkylamido, hydroxy, hydroxyalkyl, $R^{11}O$-alkyl, alkoxy, alkoxyalkyl, formamido, alkyl-$CO_2$—, formamidoalkyl, alkyl-$CO_2$-alkyl-, carboxyl, alkyl-$CO_2H$, alkyl-$O_2C$—, alkyl-$O_2C$-alkyl-, and $OR^{11}$.

In the present invention it is preferred that in the compounds of Formula I:

$R^a$ is selected from the group consisting of:
(1) hydrogen,
(2) hydroxy,
(3) $C_{1-6}$alkoxy, and
(4) —$OR^{11}$;

$R^b$ is hydrogen;

$R^c$, $R^d$, and $R^e$ are independently:
(1) —O—$R^1$, wherein $R^1$ is as defined below and
(2) hydrogen, with the provisio that at least one of $R^c$, $R^d$, and $R^e$ are other than hydrogen;

$R^f$ is hydrogen;

$R^1$ is selected from:
(1) substituted $C_{2-6}$alkyl wherein the alkyl is substituted with one or more of the substituent(s) selected from:
  (a) aryl,
  (b) substituted aryl in which the substituents are X, Y and Z,
  (c) heteroaryl,
  (d) substituted heteroaryl in which the substituents are X, Y and Z,
  (e) $C_{1-6}$alkoxy,
  (f) hydroxy,
  (g) oxo, and
  (h) —$OR^{11}$;
(2) substituted or unsubstituted $C_{2-6}$alkyl wherein one or more of the alkyl carbons is replaced by a group selected from: —$NR^6$—, —O—, —$S(O)_p$—, —$CO_2$—, —$O_2C$—, —$CONR^6$—, —$NR^6CO$—, and —$NR^6CONR^7$—, and the alkyl may be substituted with one or more of the substituent(s) selected from:
  (a) aryl,
  (b) substituted aryl in which the substituents are X, Y and Z,
  (c) heteroaryl,
  (d) substituted heteroaryl in which the substituents are X, Y and Z,
  (e) $C_{1-6}$alkoxy,
  (f) hydroxy,
  (g) oxo, and
  (h) —$OR^{11}$;
(3) substituted $C_{3-6}$alkenyl wherein the alkenyl contains one to two double bonds and the alkyl or alkenyl may be substituted with one or more of the substituent(s) selected from:
  (a) aryl,
  (b) substituted aryl in which the substituents are X, Y and Z,
  (c) heteroaryl,
  (d) substituted heteroaryl in which the substituents are X, Y and Z,
  (e) $C_{1-6}$alkoxy,
  (f) hydroxy,
  (g) oxo, and
  (h) —$OR^{11}$.

In the compound of Formula I it is also preferred that:

$R^a$ is selected from:
(1) hydroxy, and
(2) $C_{1-6}$alkoxy;

$R^2$ is selected from:
(1) hydrogen,
(2) methyl,
(3) ethyl,
(4) propyl,
(5) allyl,
(6) —$R^{11}$,
(7) —$C_{2-3}$alkyl-OH; and
(8) —$C_{2-3}$alkyl-$OR^{11}$;

$R^3$ is selected from:
(1) hydrogen,
(2) hydroxy,
(3) —$OR^{11}$, or $R^3$ and $R^4$ taken together form a double bond;

$R^{10}$ is hydrogen, hydroxy, fluoro, or —$OR^{11}$;

$R^{12}$ is hydroxy, hydrogen or with $R^{13}$ forms a double bond;

W is O or (H,H); and n is 2.

In the compound of Formula I it is even more preferred that:

$R^1$ is selected from:

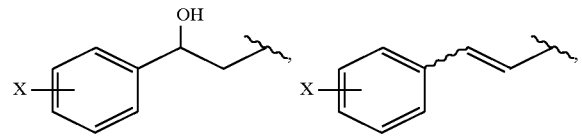

wherein X is selected from: H, 3-$CH_3$, 3-F, 4-$CH_3S$, 4-$CF_3$, 3,5-$(CH_3)_2$, 3-$NO_3$, 3-OCH3, 4-OCH3, 4-$OCH_2Ph$, 4-$OCH_2Ph$(4-$OCH_3$), 3-HOPh,

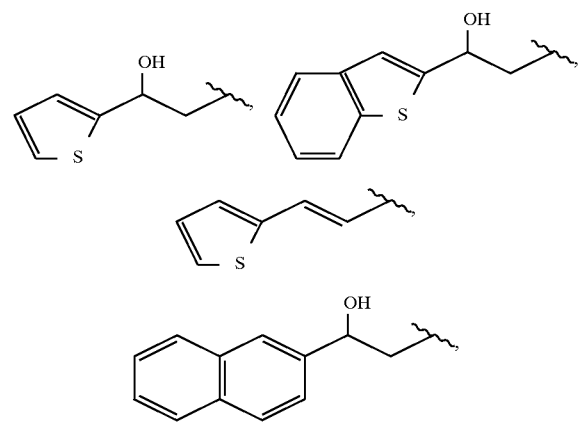

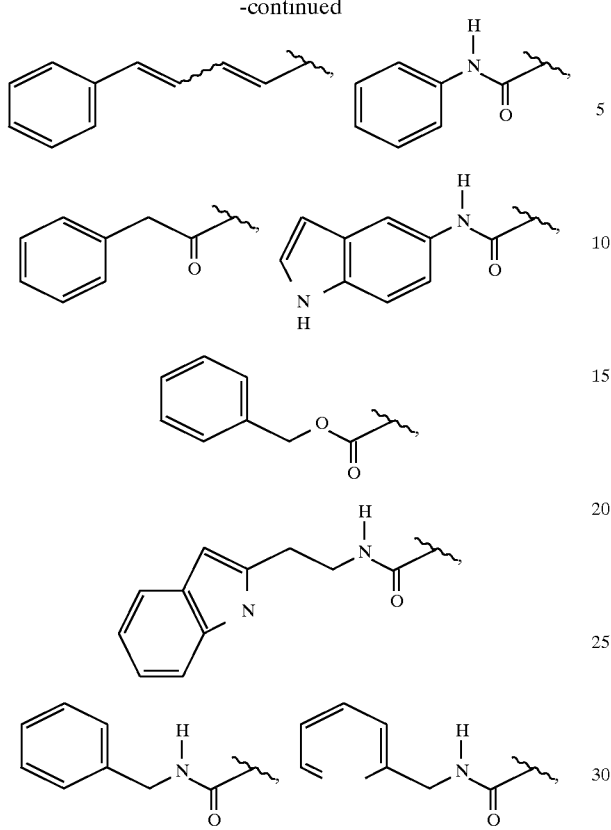
—CH$_3$,
—CH=CH$_2$,
—CH$_2$—CH=CH$_2$,
—CH$_2$CH$_2$—CH=CH$_2$,
-phenyl,
—CH$_2$-phenyl,
—CHO,
—CH$_2$CHO,
—CH$_2$CH$_2$CHO,
—CH$_2$OH,
—CH(OH)CH$_2$OH,
—CH$_2$CH(OH)CH$_2$OH, and
—CH$_2$CH$_2$CH(OH)CH$_2$OH.
The term "heteroaryl" as utilized herein is intended to include the following heteroaromatic groups which may include X, Y and Z substitution as indicated and wherein Q is —N(X)—, —O—, —S—, —SO, or —SO$_2$—:
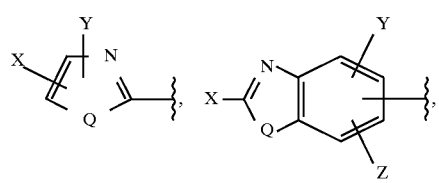
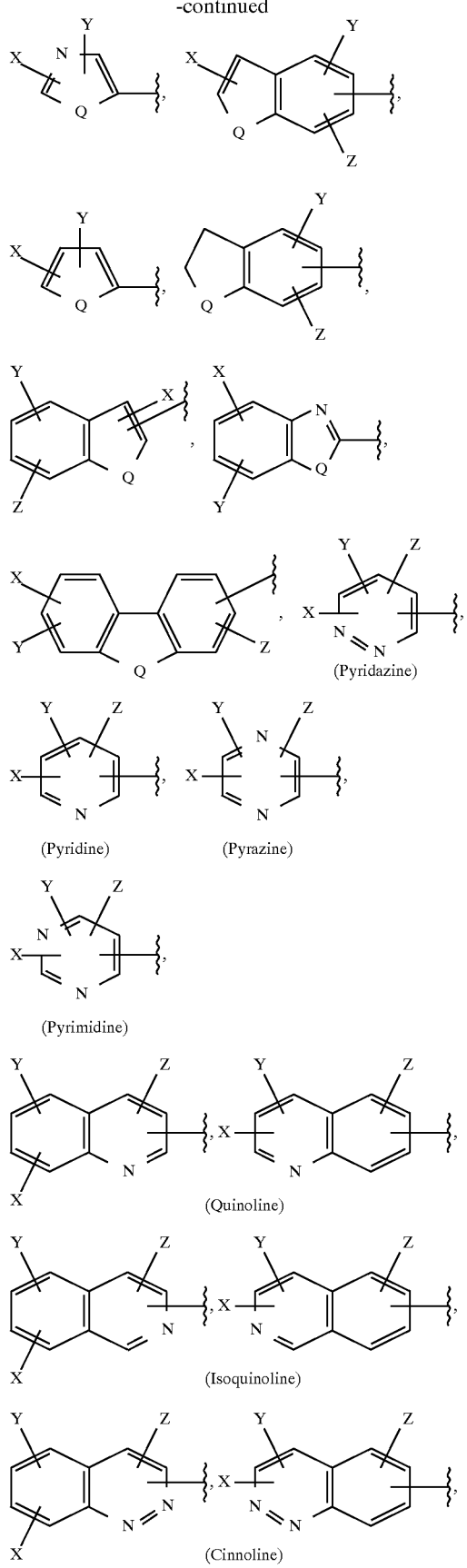

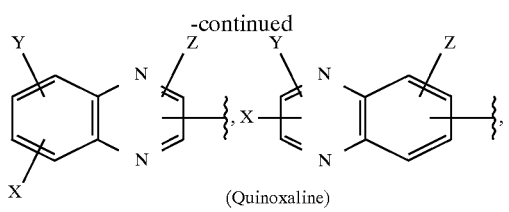

(Quinoxaline)

In the compound of Formula I it is preferred that the heteroaryl is selected from the group consisting of:

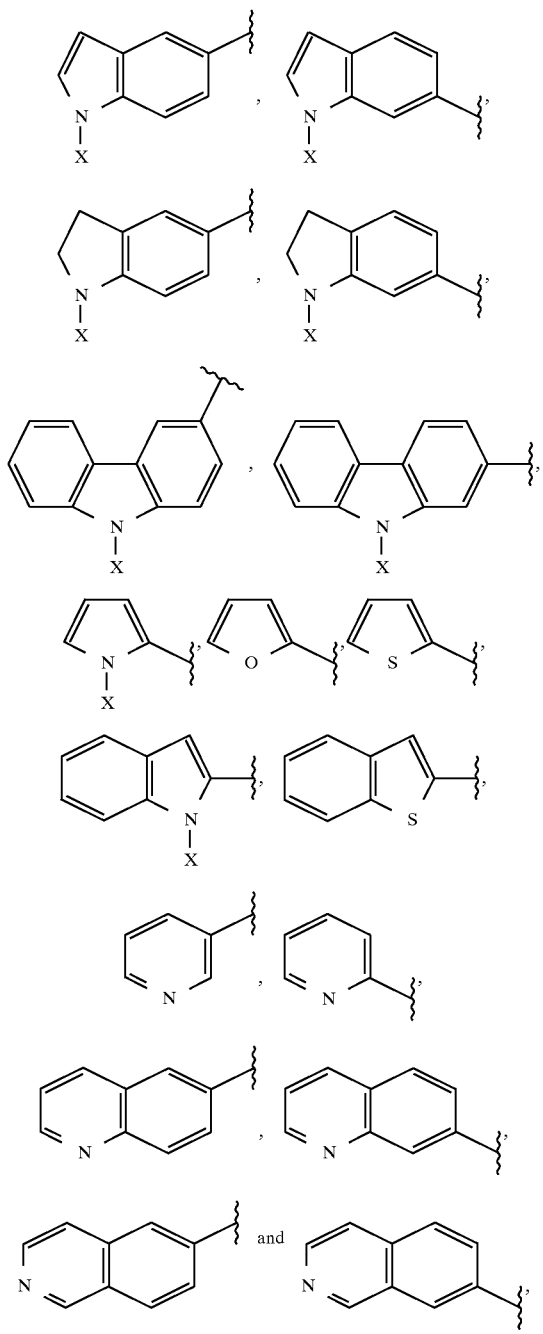

wherein X is as defined above.

Representative compounds of the present invention include the compounds identified as follows:

17-Ethyl-1,14-dihydroxy-12-[2'-(4"-oxo-3"-methoxycyclohex-5"-enyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#1)

17-Ethyl-1,14-dihydroxy-12-[2'-(4"-oxo-3"-methoxycyclohex-2"-enyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#2)

17-Ethyl-1,14-dihydroxy-12-[2'-(3"-methoxy-4",5"-dihydroxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#3)

17-Ethyl-1,14-dihydroxy-12-[2'-(3"-methoxy-4"-hydroxy-5"-(indol-5'"-yloxy)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#4)

17-Ethyl-1,14-dihydroxy-12-[2'-(3"-methoxy-4"-hydroxy-5"-(m-methoxyphenyloxy)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#5)

17-Ethyl-1,14-dihydroxy-12-[2'-(3"-methoxy-4"-hydroxy-5"-(p-biphenyloxy)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#6)

17-Ethyl-1,14-dihydroxy-12-[2'-(3"-methoxy-4"-hydroxy-5"-(p-hydroxyphenyloxy)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#7)

17-Ethyl-1,14-dihydroxy-12-[2'-(3"-methoxy-4"-hydroxy-5"-(p-tolyloxy)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#8)

17-Ethyl-1,14-dihydroxy-12-[2'-(3"-methoxy-4"-hydroxy-5"-(p-hydroxyethylphenyloxy)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#9)

17-Ethyl-1,14-dihydroxy-12-[2'-(3"-methoxy-4"-hydroxy-5"-(o-fluoro-phenyloxy)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#10)

17-Ethyl-1,14-dihydroxy-12-[2'-(3"-methoxy-4",5"-bisallyloxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#11)

17-Ethyl-1,14-dihydroxy-12-[2'-(3"-methoxy-4"-hydroxy-5"-allyloxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#12)

17-Ethyl-1,14-dihydroxy-12-[2'-(3"-methoxy-4"-allyloxy-5"-hydroxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#13)

17-Ethyl-1,14-dihydroxy-12-[2'-(3"-methoxy-4",5"-bisbenzyloxycyclohexyl)-1'-methylvinyl]-23,25-dimethoxy-13,19,21,27-tetramethyl-11,28-dioxa-4- azatricylclo[22.3.1.0$^{4,9}$]octacos-18-ene-2,3,10,16-tetraone; (#14)

17-Ethyl-1,14-dihydroxy-12-[2'-(3"-methoxy-4"-hydroxy-5"-benzyloxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#15)

17-Ethyl-1,14-dihydroxy-12-[2'-(3"-methoxy-4"-benzyloxy-5"-hydroxycyclohexyl)-1'-methylvinyl]-23,25-dimethoxy-13,19,21,27-tetramethyl-11,28-dioxa-4-azatricylclo-[22.3.1.0$^{4,9}$]octacos-18-ene-2,3,10,16-tetraone; (#16)

17-Ethyl-1-hydroxy-12-[2'-(3",4"-bisoxocyclohexyl)-1'-methylvinyl]-23,25-dimethoxy-13,19,21,27-tetramethyl-11,28-dioxa-4-aza-tricylclo[22.3.1.0$^{4,9}$]octacos-18-ene-2,3,10,16-tetraone; (#17)

17-Ethyl-1,14-dihydroxy-12-[2'-(3"-methoxy-4",5"-bisoxocyclohexyl)-1'-methylvinyl]-23,25-dimethoxy-13,19,21,27-tetramethyl-11,28-dioxa-4-azatricylclo [22.3.1.0$^{4,9}$]octacos-18-ene-2,3,10,16-tetraone; (#18)

17-Ethyl-1,14-dihydroxy-12-[2'-(4"-oxo-3"-methoxycyclohex-5"-enyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#19)

17-Ethyl-14-dihydroxy-12-[2'-(3"-methoxy-4"-oxo-6"-ethylaminocyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#20)

or a pharmaceutically acceptable salt thereof.

B. Preparation of Compounds Within the Scope of the Present Invention

The starting materials for the preparation of the compounds of this invention are represented by Formula II:

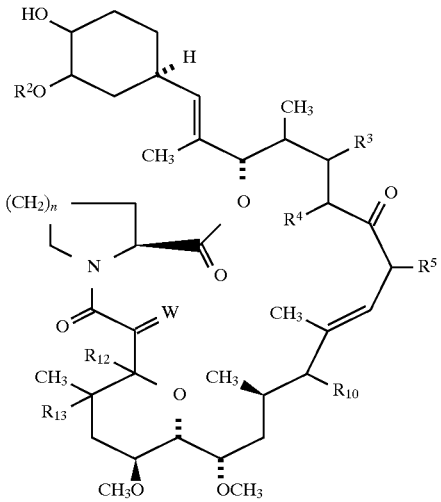

wherein:

$R^2$ is hydrogen or methyl;

$R^3$ is hydrogen, hydroxy, or $C_{1-6}$ alkoxy;

$R^4$ is hydrogen, or $R^3$ and $R^4$ taken together form a double bond;

$R^5$ is methyl, ethyl, propyl or allyl;

$R^{10}$ is hydrogen, hydroxy or fluoro;

$R^{12}$ is hydrogen, hydroxy, $R^{12}$ is hydrogen or $R^{12}$ and $R^{13}$ taken together form a double bond;

W is O, (H, OH) or (H,H); and n is 1 or 2.

The production and characterization of compounds of Formula II is well known in the literature (see U.S. Pat. No. 4,894,366 issued Jan. 16, 1990; U.S. Pat. No. 4,929,611 issued May 29, 1990; U.S. Pat. No. 3,244,592 issued Apr. 15, 1966; EPO Publication No. 0,323,042; EPO Publication No. 0,356,399; PBJ Disclosure 63-17884; *J. Am. Chem. Soc.*, 1987, 109, 5031; *J. Antibiotics*, 1987, 40, 1249, *J. Antibiotics*, 1988, 41(11), 1592; and *J. Antibiotics*, 1992, 45(1), 118). Both biological fermentation and synthetic processes may be found. A synthetic route to compounds of Formula II can involve modifications of a route described in *J. Am. Chem. Soc.*, 1989, 111, 1157.

Biological fermentation followed by synthetic modification is presently favored in the art as the method to produce compounds of Formula II. Organisms belonging to the genus Streptomyces such as *Streptomyces tsukabaensis*, No. 9993 and *Streptomyces hygroscopicus*, var. *ascomycetis*, No. 14891 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where $R^2$ is methyl, W is O, $R^3$ is hydroxyl, $R^4$ is hydrogen, $R^5$ is allyl and n is 2; (B) where $R^2$ is methyl, W is O, $R^3$ is hydroxyl, $R^4$ is hydrogen, $R^5$ is ethyl and n is 2; (C) where $R^2$ is methyl, W is O, $R^3$ is hydroxyl, $R^4$ is hydrogen, $R^5$ is methyl and n is 2; and (D) where $R^2$ is methyl, W is O, $R^3$ is hydroxyl, $R^4$ is hydrogen, $R^5$ is allyl and n is 1.

A lyophilized sample of the isolated *Streptomyces tsukubaensis*, No. 9993 was deposited with the Fermentation Research Institute, Agency of Industrial Science and Technology (No. 1—3, Higashi 1-chome, Yatabemachi Tsukuba-gun, Ibaraki Prefecture, Japan) under the deposit number of FERM P-7886 (deposit date: Oct. 5th, 1984), and then converted to Budapest Treaty route of the same depository on Oct. 19, 1985 under the new deposit number of FERM BP-927.

Using the four compounds produced in fermentation above, the remaining compounds of Formula II may be easily produced. The allyl of $R^5$ may be conveniently reduced to propyl by well known methods, for example as described in U.S. Pat. No. 4,894,366. The hydroxy of $R^3$ may be protected by well known methods, for example as disclosed in EPO Publication No. 0,323,042. Likewise, the hydroxyl at C-4" may also be protected. In addition, the hydroxy of $R^3$ may be reduced to a hydrogen or eliminated to form a double bond with $R^4$ (by methods disclosed in U.S. Pat. No. 4,894,366, EPO Publication No. 0,323,042 or EPO Publication No. 0,413,532). The carbonyl of W may be reduced to the alcohol by methods disclosed in EPO Publication No. 0,323,042 or by methods disclosed in EPO Publication No. 0,445,975.

The methyl of E as produced may be replaced with hydrogen or demethylated and subsequently protected as desired, if necessary. This demethylation of compounds wherein E is methyl may be carried out in a fermentation reaction using the compounds of Formula II as a feedstock. For instance, compound A named under Formula II above may be demethylated at E above by using the microorganism Actinomycetales ATCC No. 53771 (described in U.S. Pat. No. 4,981,792) or by using the microorganism *Streptomyces tsukubaensis*, No. 9993 (described in EPO Publication No. 0,353,678). Similarly, compound B named under Formula II above may be demethylated at E above using the microorganism Actinoplanacete sp. ATCC No. 53771 (described in EPO Publication No. 0,349,061). In addition the compound of Formula II wherein E is H, W is O, $R^3$ is hydroxy, $R^4$ is hydrogen, $R^5$ is ethyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (as described in EPO Publication No. 0,388,152). Similarly, the compound of Formula II wherein E is hydrogen, W is O, $R^3$ is hydroxy, $R^4$ is hydrogen, $R^5$ is methyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (EPO Publication No. 0,388, 153). The hydroxy of C-3" may be protected by methods similar to those known for the protection of the hydroxyl groups of $R^3$ and/or C-4", for example as disclosed in U.S. Pat. No. 4,894,366.

Suitable protecting groups for hydroxyl include those groups well known in the art such as: methylthiomethyl, ethylthiomethyl; trisubstituted silyl such as trimethylsilyl, triethylsilyl, tributylsilyl, tri-i-propylsilyl, t-butyldimethylsilyl, tri-t-butylsilyl, methyl-diphenylsilyl, ethyldiphenylsilyl, t-butyldiphenylsilyl, and the like; acyl such as acetyl, pivaloyl benzoyl, 4-methoxybenzoyl, 4-nitrobenzoyl and aliphatic acyl substituted with aromatic group, which are derived from carboxylic acids; and the like.

Compounds A, B, C and D of Formula II, organisms to produce the same, conditions of fermentation, separation techniques, and chemical modification of the products are fully described in U.S. Pat. No. 4,894,366, dated Jan. 16, 1990, U.S. Pat. No. 4,929,611, issued May 29, 1990 and U.S. Pat. No. 5,110,811, issued May 5, 1992.

The novel processes for preparing the novel compounds of the present invention are illustrated as follows, wherein R, $R^1$, $R^2$, $R^3$, $R^5$, $R^6$, $R^7$, $R^8$, $R^9$, $R^{10}$, $R^{11}$, $R^{12}$, $R^{13}$, W and n are as defined above unless otherwise indicated. It will be readily apparent to one of ordinary skill in the art reviewing the synthetic route depicted below that other compounds within Formula I can be synthesized by substitution of appropriate reactants and agents in the synthesis shown below.

REACTION SCHEME A

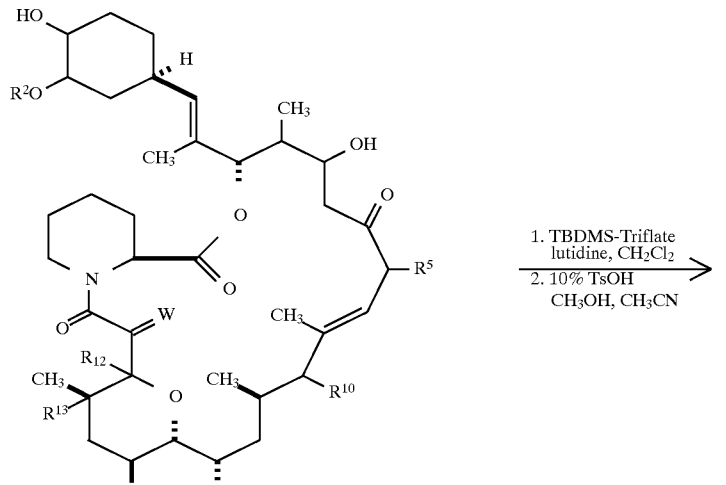

1

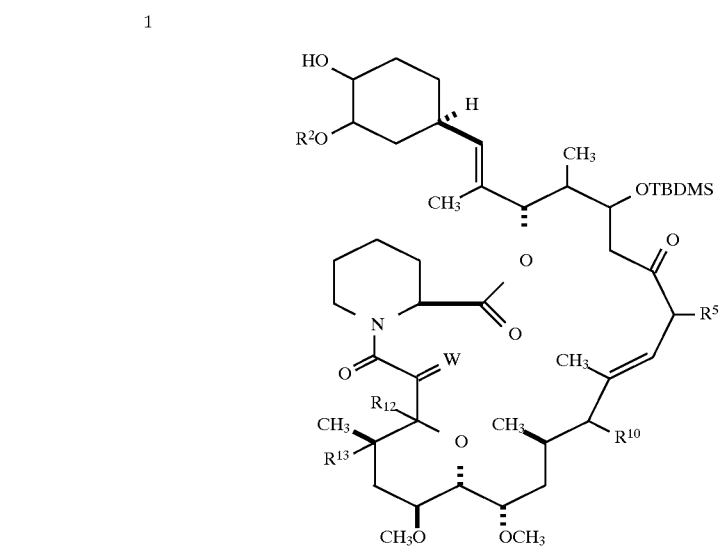

2

REACTION SCHEME B
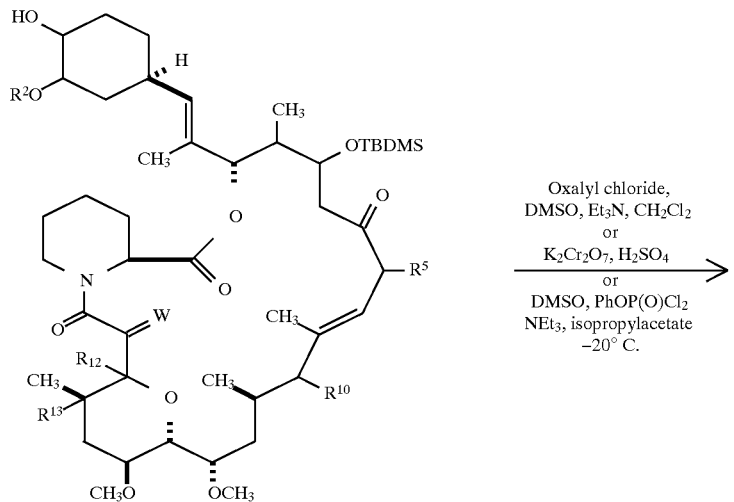
2
Oxalyl chloride,
DMSO, Et₃N, CH₂Cl₂
or
K₂Cr₂O₇, H₂SO₄
or
DMSO, PhOP(O)Cl₂
NEt₃, isopropylacetate
−20° C.
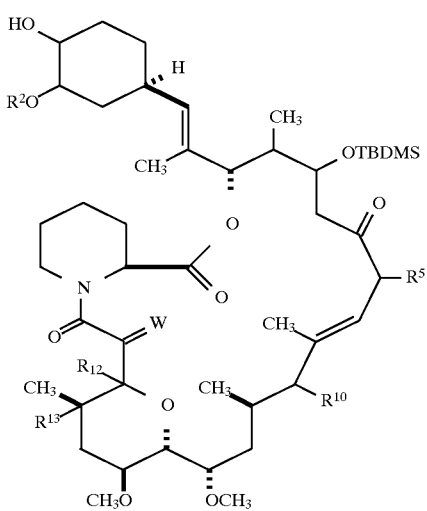
3

REACTION SCHEME C
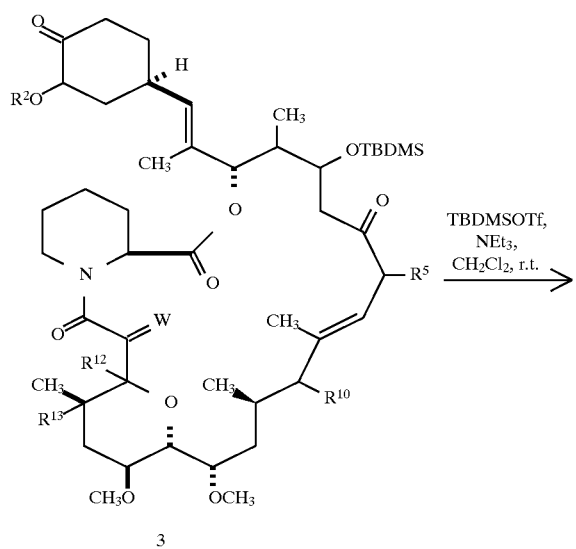
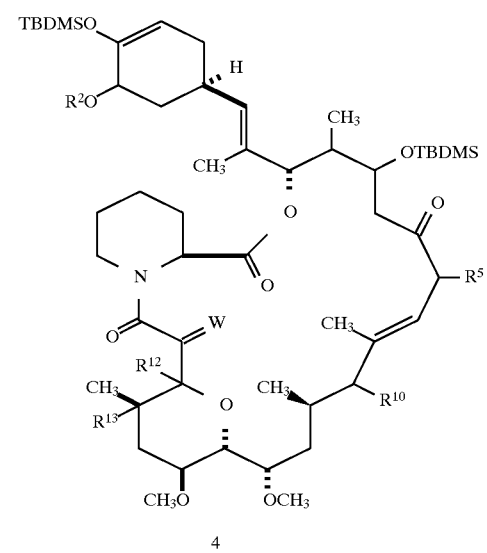
REACTION SCHEME D
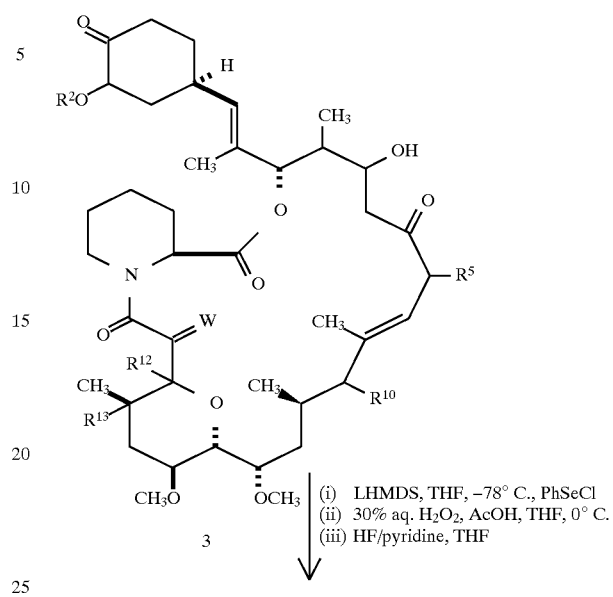
(i) LHMDS, THF, −78° C., PhSeCl
(ii) 30% aq. H₂O₂, AcOH, THF, 0° C.
(iii) HF/pyridine, THF

-continued
REACTION SCHEME D
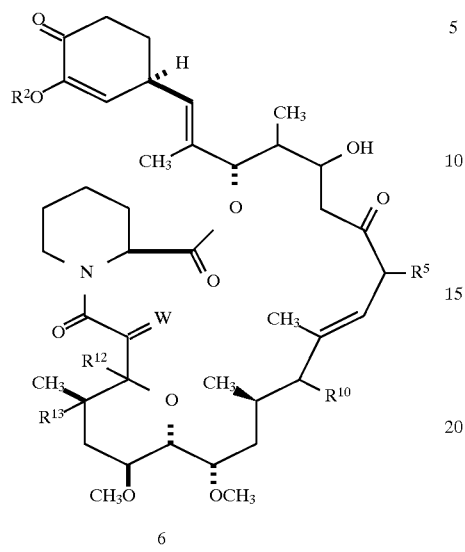
6
REACTION SCHEME E
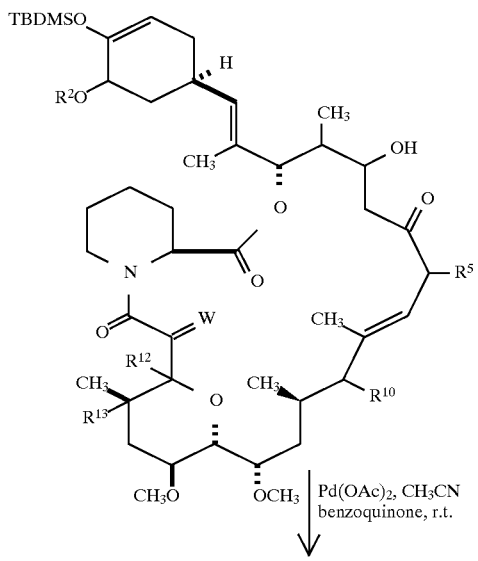
Pd(OAc)₂, CH₃CN
benzoquinone, r.t.
-continued
REACTION SCHEME E
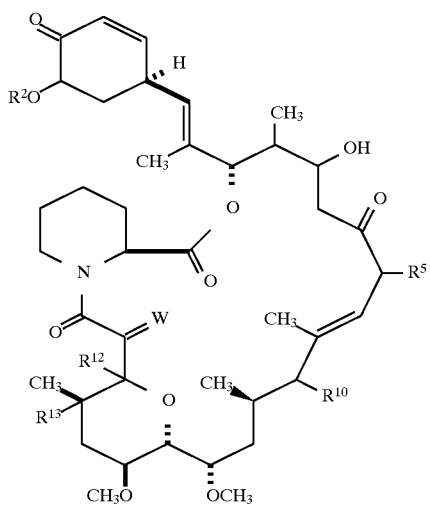
REACTION SCHEME F(1)
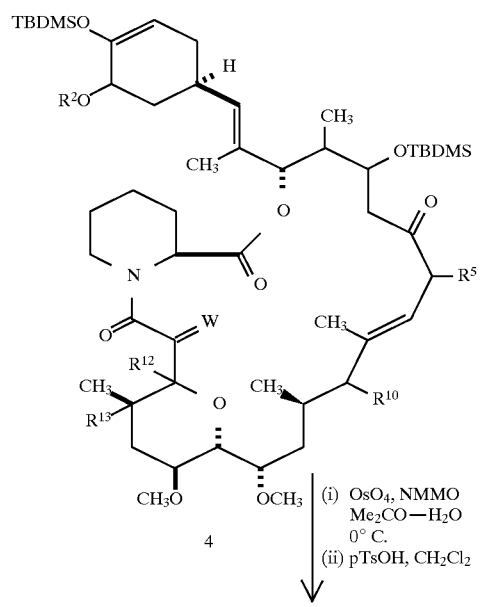
4
(i) OsO₄, NMMO
Me₂CO—H₂O
0° C.
(ii) pTsOH, CH₂Cl₂

29
-continued
REACTION SCHEME F(1)
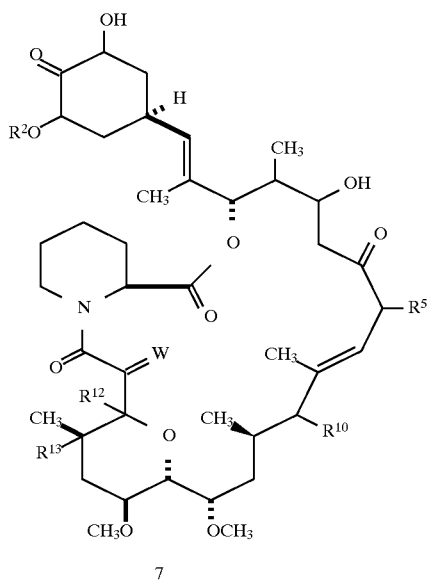
7
REACTION SCHEME F(2)
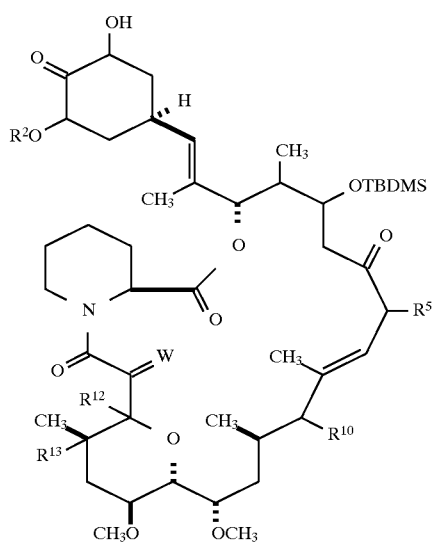
7 | (i) NaBH(OAc)$_3$,
AcOH/Me$_2$CO, −15° C.
(ii) HF/pyridine, THF
30
-continued
REACTION SCHEME F(2)
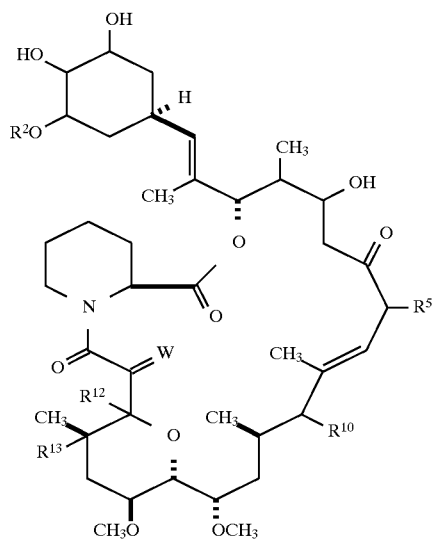
8
REACTION SCHEME G
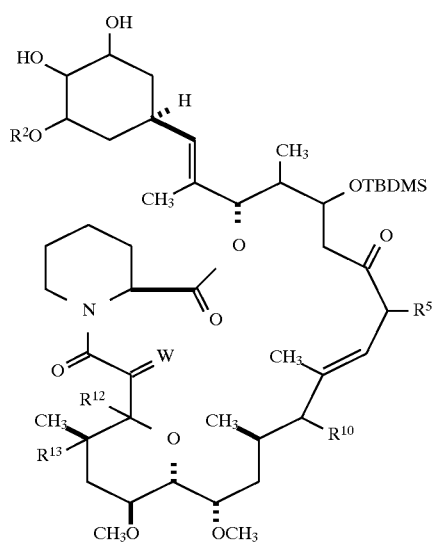
8 | (i) Ar$_3$Bi, CH$_3$CO$_3$H,
40° C., CH$_2$Cl$_2$
(ii) HF/pyridine, THF

REACTION SCHEME G
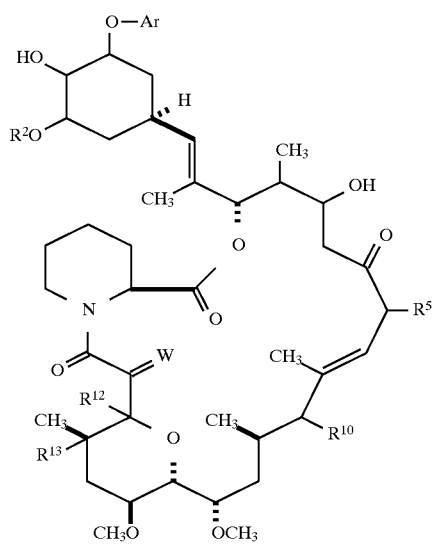
REACTION SCHEME H
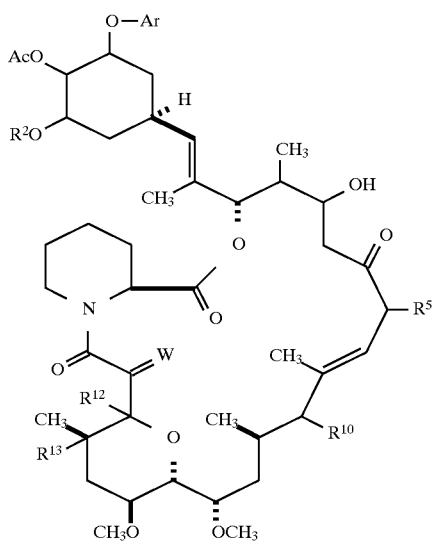
REACTION SCHEME H
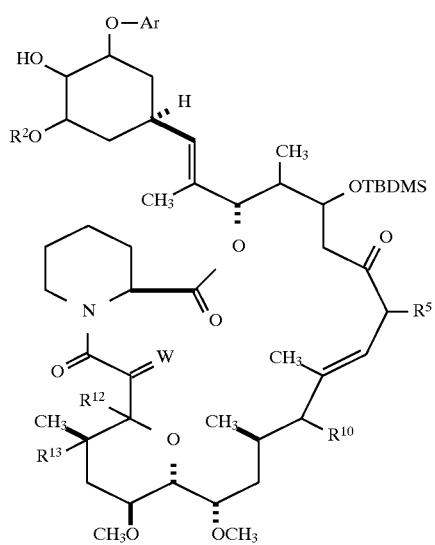
Ac₂O, NEt₃, DMAP
CH₂Cl₂, 0° C.

REACTION SCHEME I
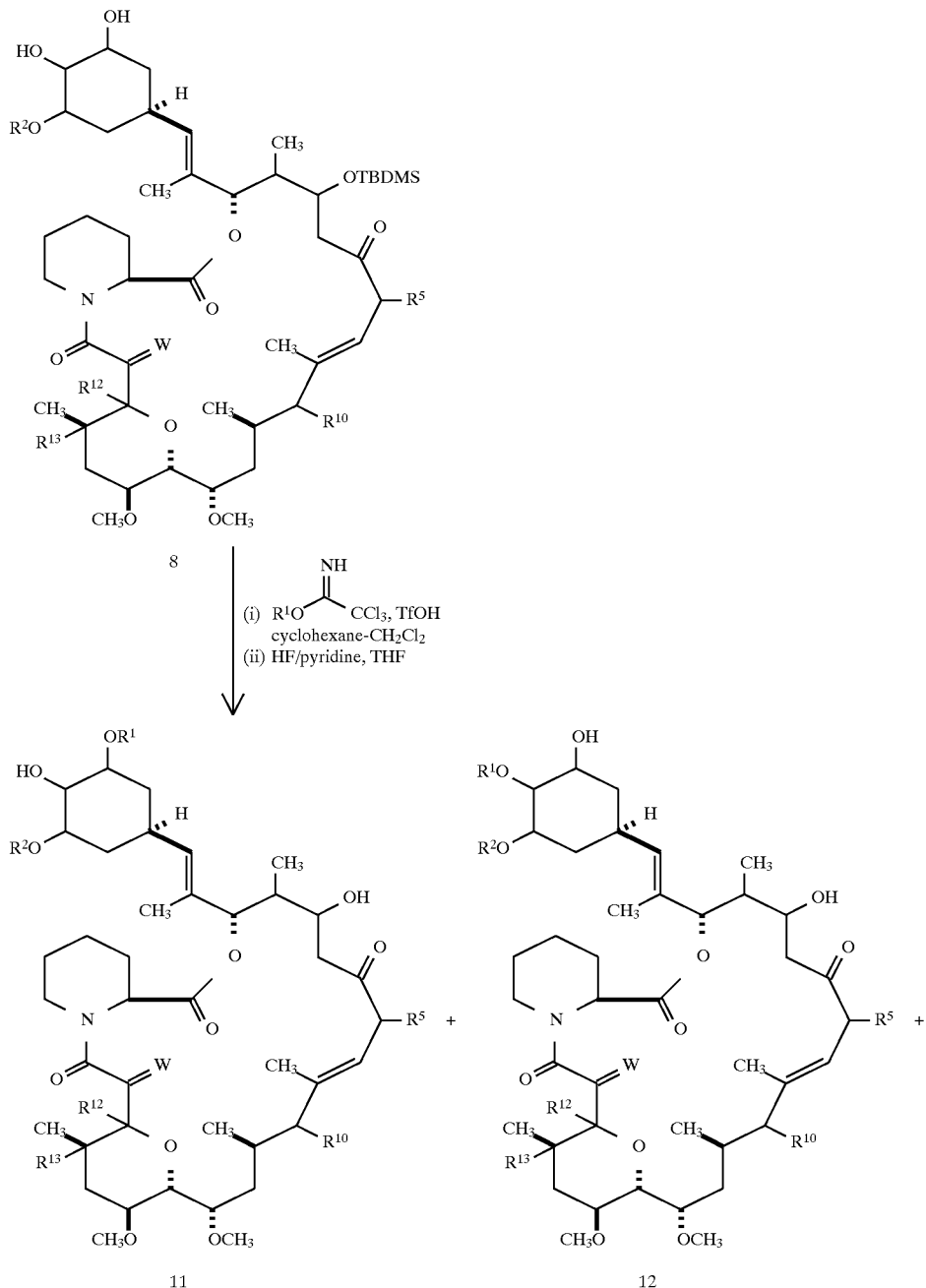

-continued
REACTION SCHEME I
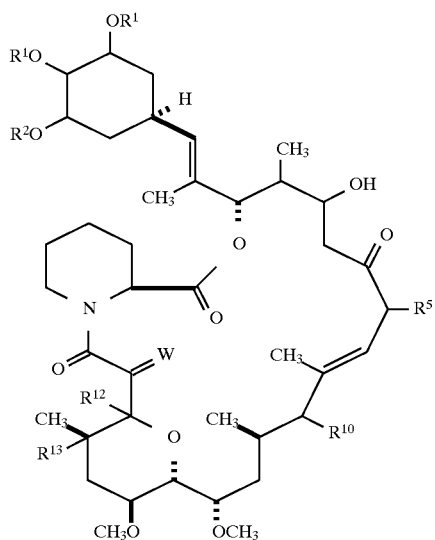
13
REACTION SCHEME J
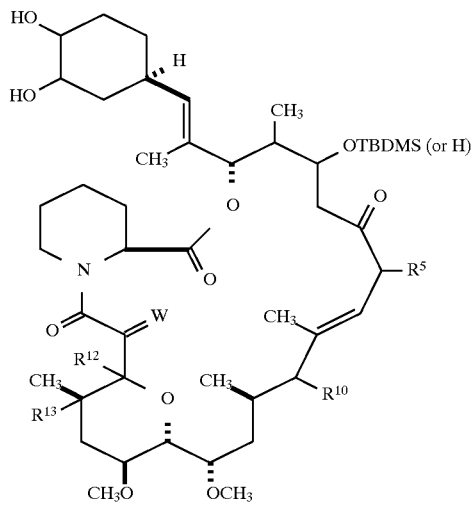
2
DMSO, PhOP(O)Cl$_2$
NEt$_3$, isopropylacetate
−20° C.
-continued
REACTION SCHEME J
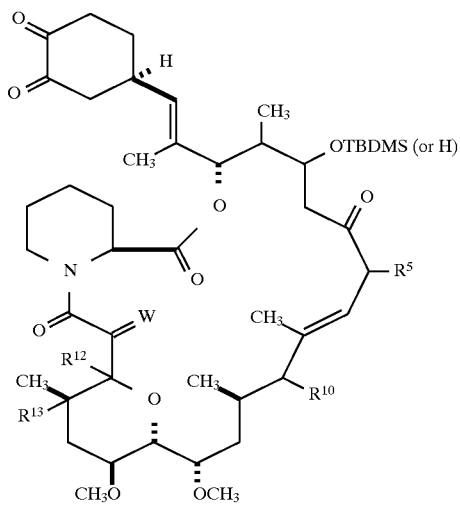
14

REACTION SCHEME K
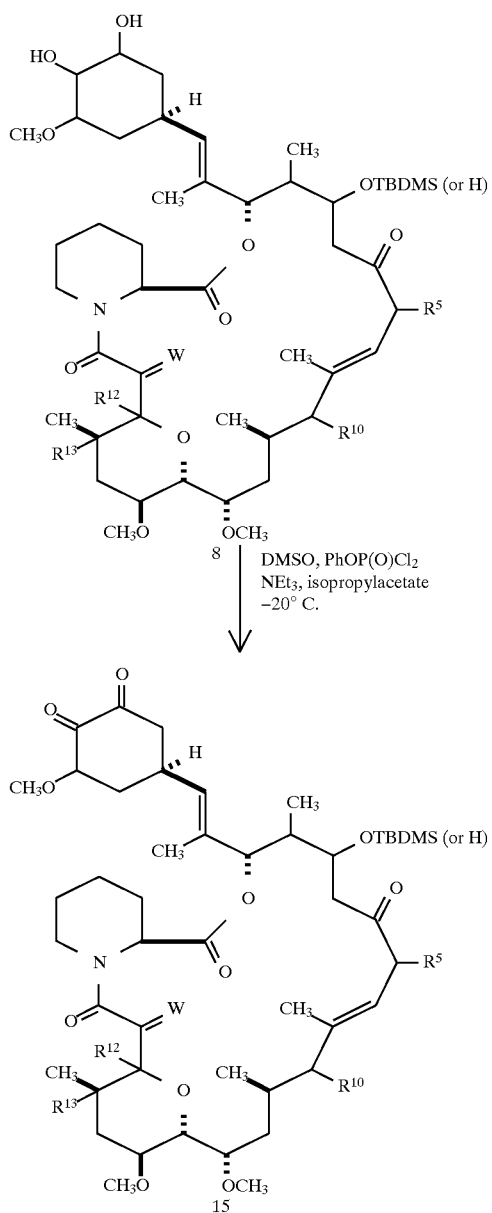
REACTION SCHEME L
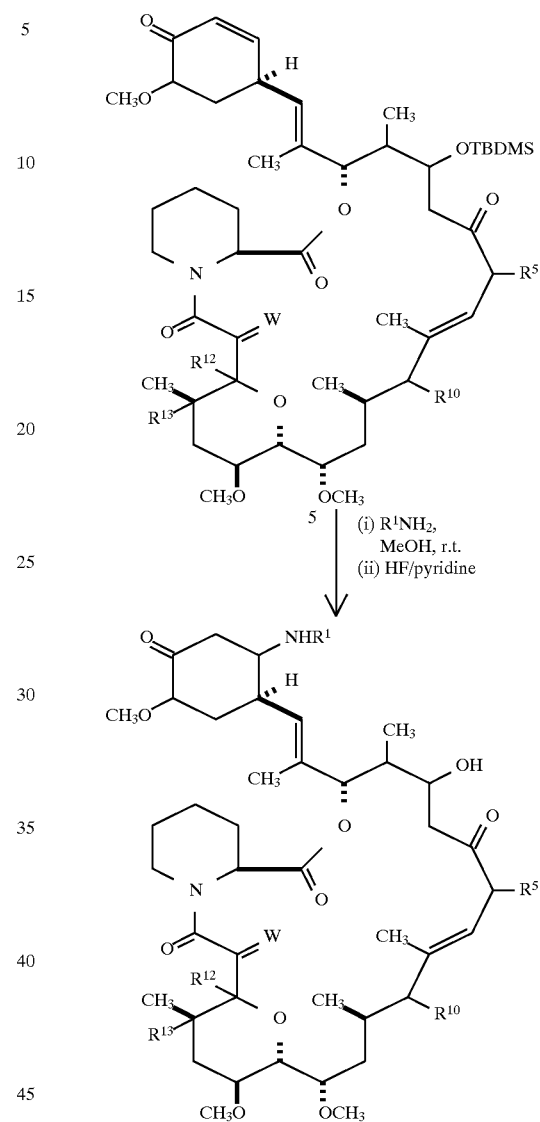

REACTION SCHEME M
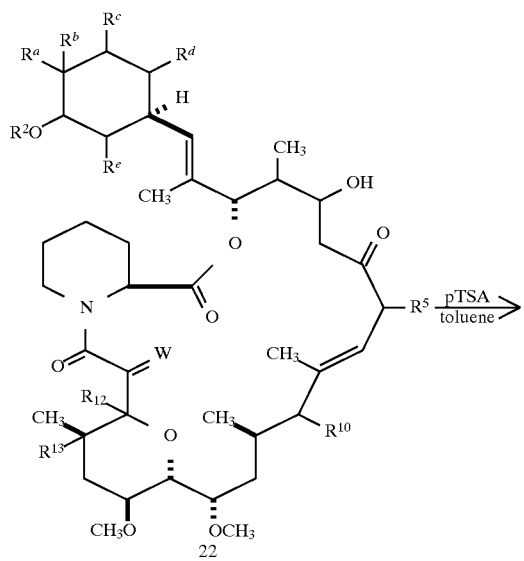
22
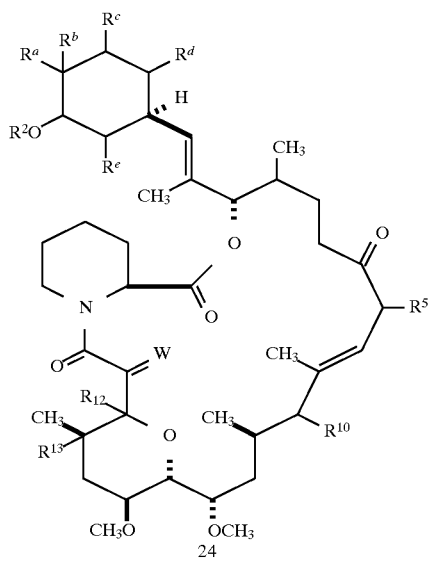
24
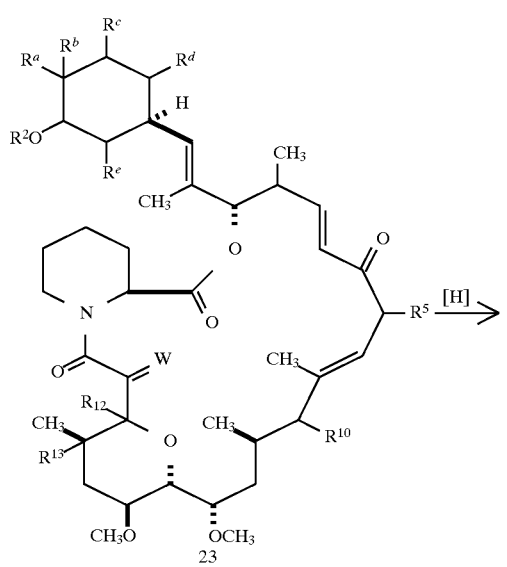
23
-continued
REACTION SCHEME M REACTION SCHEME N
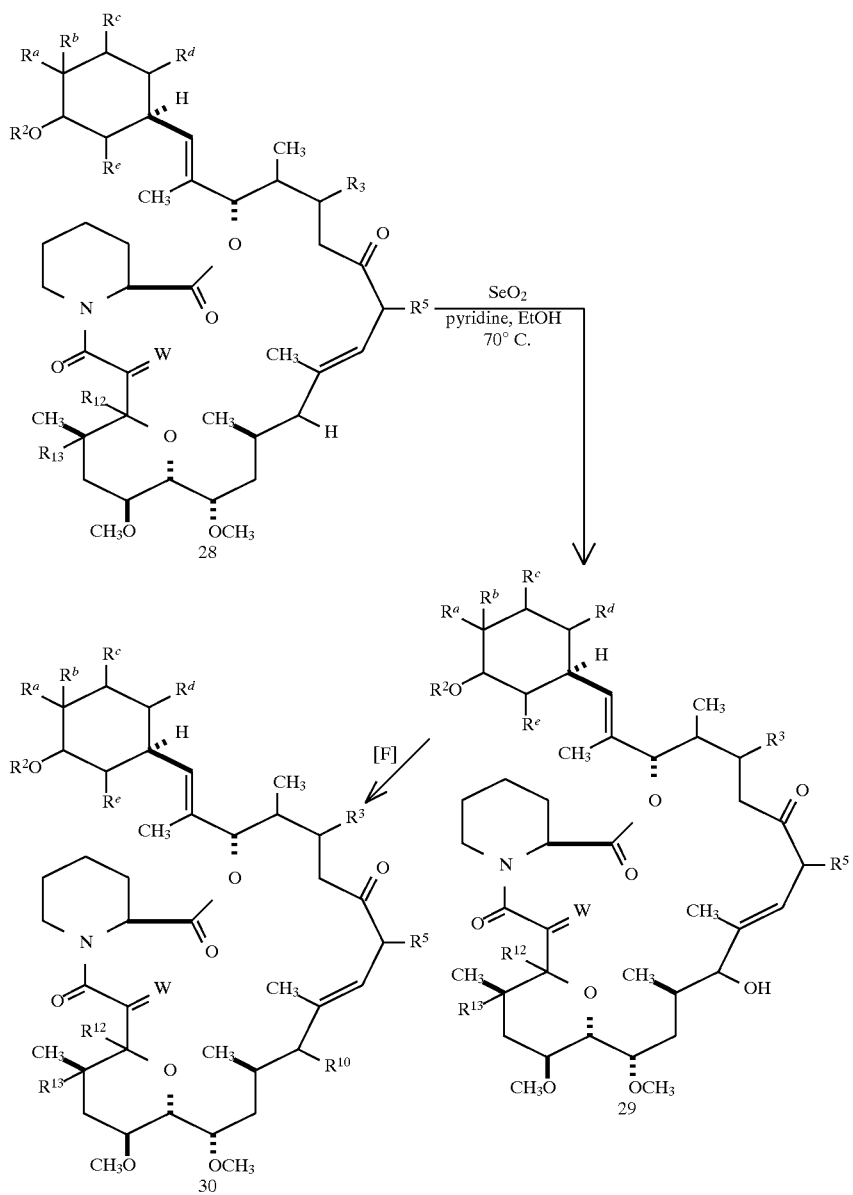

REACTION SCHEME O
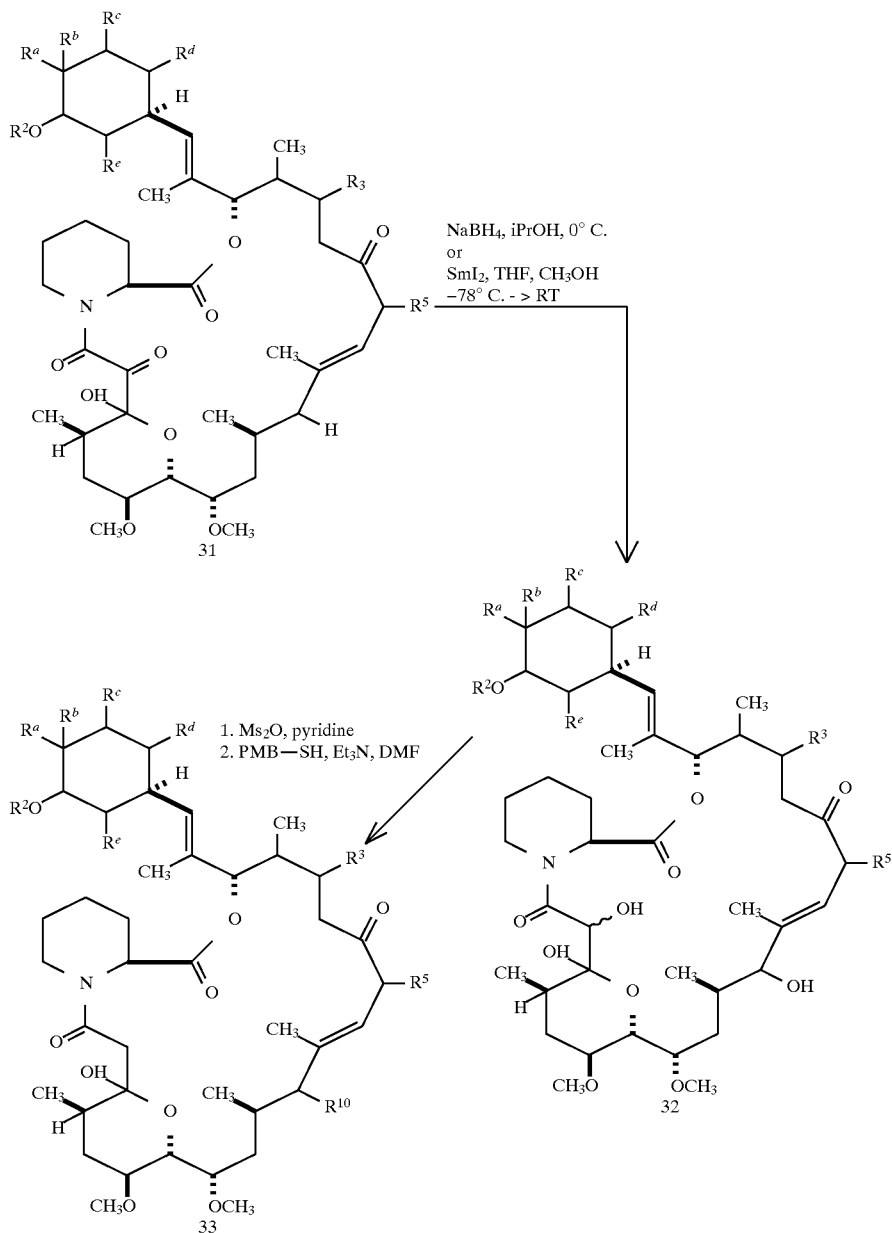

REACTION SCHEME P
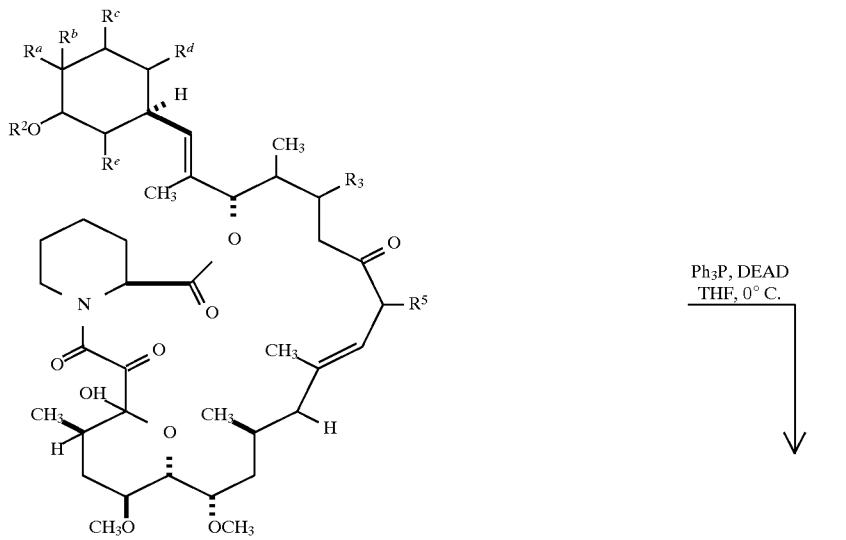
34
Ph₃P, DEAD
THF, 0° C.
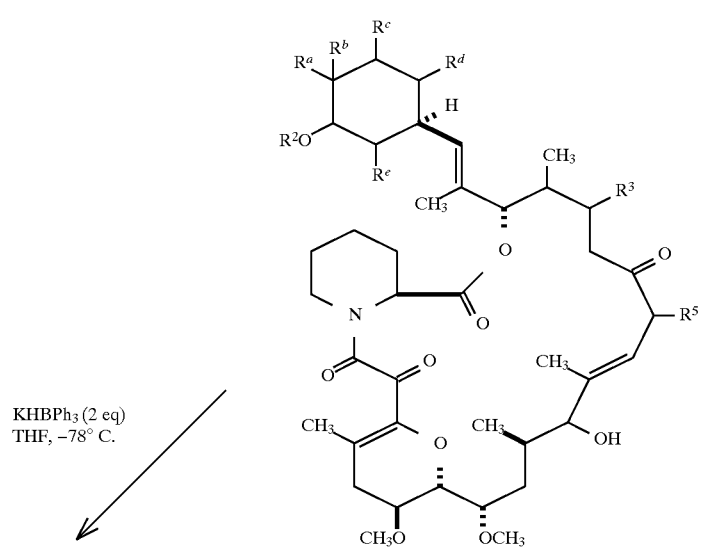
35
KHBPh₃ (2 eq)
THF, −78° C.

-continued
REACTION SCHEME P

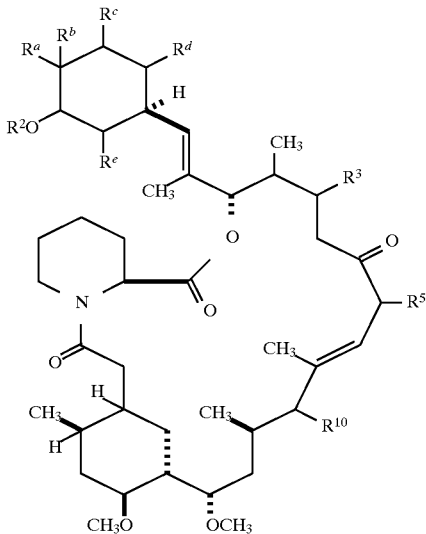

36

Reaction Scheme A

Protection of the C-3", C-4" and/or the C-14 hydroxyl group(s) may be accomplished by methods known in the art for compounds of Formula II such as by treatment with: 2,6-lutidine and triisopropylsilyl trifluoromethanesulfonate in a solution of methylene chloride; 2,6-lutidine and t-butyldimethylsilyl trifluoromethanesulfonate in a solution of methylene chloride; pyridine and acetic anhydride in a solution of methylene chloride; pyridine and benzoyl chloride in a solution of dichloromethane; pyridine and p-nitrobenzoyl chloride in a solution of dichloromethane; imidazole and t-butyldiphenylsilyl chloride in a solution of methylene chloride; and the like. For example, as shown in Reaction Scheme A, the C-4",14-dihydroxy-C-3"-methoxy macrolide 2 may be protected at C-14 as the t-butyldimethylsilyl ether by treatment with t-butyldimethylsilyl trifluoromethanesulfonate in methylene chloride to give the C-4",14-di-O-TBDMS macrolide. Treatment with toluenesulfonic acid in methanol results in selective removal of the C-4" silyl ether to give the C-14-O-TBDMS macrolide 3. An alternative method employs 2.5% HF in acetonitrile at 0° C.

Reaction Scheme B

A key intermediate for the compounds claimed herein is ketone 3 which is easily prepared by oxidation of alcohol 2. A variety of methods may be successfully employed to achieve ketone 3. They include use of the Swern reaction (oxalyl chloride, DMSO and triethylamine ($Et_3N$) in methylene chloride). Another reagent that works very well is commonly called the Jones reagent. This is a solution of chromic acid and sulfuric acid in $H_2O$.

Reaction Scheme C

As shown in Reaction Scheme C, formation of silyl enol ethers may be accomplished by methods known in the art for compounds such as ketone 3 by treatment with tert-butyldimethylsilyl trifluoromethanesulfonate and triethylamine in an inert solvent such as methylene chloride at ambient temperature. Other trialkylsilyl trifluoromethansulfonates may also be used, such as triisopropylsilyl trifluoromethanesulfonate and the like.

Reaction Scheme D

As shown in Reaction Scheme D, enones 5 and 6 may be prepared. A solution of the ketone in a solvent such as tetrahydrofuran, ether or dimethoxyethane is treated with lithium hexamethyldisilazide or lithium diisopropylamide or other lithiated amine bases at temperatures lower than −30° C. for up to an hour, but preferably for 30 minutes. The reaction mixture may then be quenched with phenylselenyl chloride or other commonly used selenating agents such as N-phenylselenophthaimide and the like, to give intermediate selenides. These may be eliminated by most methods commonly used to oxidize selenides to selenoxides such as treatment with aqueous hydrogen peroxide or peracetic acid or dimethlydioxirane and the like in a solvent such as tetrahydrofuran at temperatures between −30° C. and ambient temperature.

Reaction Scheme E

As shown in Reaction Scheme E, the enone can also be prepared by treatment of a silyl enol ether such as 4 with palladium (II) acetate and benzoquinone in acetonitrile. This procedure can also be carried out with a trimethylsilylenol ether or a triisopropylsilyl enol ether. Also, this procedure is not restricted to the use of palladium (II) acetate and benzoquinone. The transformation can also be accomplished by using palladium (II) acetate alone, benzoquionone alone, or other palladium catalysts such as bis(acetonitrile) palladium (II) chloride and the like.

Reaction Scheme F

As shown in Reaction Scheme, the silyl enol ether 4 can be oxidized to the α-hydroxy ketone using osmium tetroxide catalyst with N-methylmorpholine N-oxide as co-oxidant followed by hydrolysis of the intermediate adduct with p-toluenesulfonic acid or other acids such as camphorsulfonic acid, methanesulfonic acid and the like in an inert solvent such as methylene chloride, benzene, toluene and the like at ambient temperature. The α-hydroxy ketone so produced can be reduced to the diol 8 by, but not restricted to, sodiumtriacetoxy borohydride. Other reducing agents can also be used such as potassiumtriphenyl borohydride, sodium borohydride, diisobutylaluminum hydride and the like.

Reaction Scheme G

As shown in Reaction Scheme G, aryl or heteroaryl ether derivatives may be prepared. A solution of the alcohol in an inert organic solvent such as methylene chloride, benzene, toluene, chloroform, or the like or mixtures thereof is treated with a triaryl- or triheteroarylbismuth diacetate reagent (prepared immediately prior to use by the addition of acetic acid to a suspension of a triaryl- or triheteroarylbismuth carbonate in an inert organic solvent such as methylene chloride, choroform or the like or mixture thereof) in the presence of a catalytic amount of copper(II) acetate at a temperature of 20°–50° C., preferably room temperature, for a period of one hour to seven days, preferably one day, to give the O-aryl or heteroaryl derivative. For example, compounds wherein Ar is 5-(1-methyl)indolyl, m-methoxyphenyl, p-biphenyl, p-hydroxyphenyl, p-tolyl, o-fluorophenyl, p-(2-hydroxyethyl)phenyl may be prepared. Alternatively, the triaryl- or triheteroaryl-bismuth(V) reagent may be prepared by treatment of a triaryl- or triheteroarylbismuthine with a suitable oxidant such as peracetic acid, iodobenzene diacetate, bis(trifluoroacetoxy) iodobenzene and the like in an inert solvent such as methylene chloride, chloroform, benzene, toluene and the like. The triaryl- or triheteroarylbismuth(V) reagent may be used without purification or may be purified by silica gel chromatography. Triaryl- or triheteroarylbismuthines may be prepared by the reaction of an appropriate aryl or heteroaryl grignard reagent with bismuth trichloride in an inert organic solvent such as tetrahydrofuran, diethyl ether, or 1,4-dioxane, or mixtures thereof, at or near room temperature for a period of 1 to 48 hours. General procedures for the preparation and use of triheteroaryl bismuth reagents may be found in Barton, D. H. E., et al., *J. Chem. Soc. Chem. Commun.*, 65, 1986 and references cited therein.

Reaction Scheme H

As shown in Scheme H, aryl ethers such as 9 may be acetylated using any of the commonly used procedures for making acetates such as the one shown in the scheme. Here the aryl ether, in an inert solvent such as methylene chloride, benzene, toluene, chloroform and the like, can be treated with acetic anhydride and triethylamine with catalytic 4-dimethylaminopyridine at temperatures between –30° C. and ambient temperature for a period of 45 minutes. Acetyl chloride and the like may also be used as acetylating agents and pyridine or other amine bases can be used as the base.

Reaction Scheme I

As shown in Reaction Scheme I, C-32 and C-33 (and also C-30 and C-34) may be modified in any number of ways utilizing benzyl or alkenyl trichloroacetimidate reagents (i.e. $R^1$ may be allyl or benzyl). The hydroxy group may be reacted in an inert organic solvent such as methylene chloride, chloroform, pentane, hexane, cyclohexane, heptane or mixtures thereof with a heteroarylalkyl, heteroarylalkenyl or heteroarylalkynyl trichlioroacetimidate reagent (prepared by the reaction of an appropriate sodium alkoxide with trichloroacetonitrile, such as described by Wessel, H. P., Iversen, T., Bundle, D. R., *J. Chem. Soc., Perkin Trans. I*, 1985, 2247) in the presence of a mild acid catalyst such as trifluoro-methanesulfonic acid, p-toluenesulfonic acid, methanesulfonic acid, or mixtures thereof at a temperature of 20°–50° C. for a period of from one hour to seven days to give the O-alkyl-macrolides.

Reaction Scheme J

As shown in Reaction Scheme J, the dione 14 may prepared by oxidation of the diol 2. A variety of methods may be successfully employed to achieve dione 14. They include use of a modified Swern reaction (employing phenyldichlorophosphate, DMSO and triethylamine ($Et_3N$) in isopropylacetate) or a Swern reaction (oxalyl chloride, DMSO and triethylamine ($Et_3N$) in methylene chloride). Another reagent that may be employed is the Jones reagent, a solution of chromic acid and sulfuric acid in $H_2O$.

Reaction Scheme K

As shown in Reaction Scheme J, the methoxy dione 15 may prepared by oxidation of the methoxy diol 8. A variety of methods may be successfully employed to achieve the methoxy dione 15. They include use of a modified Swern reaction (employing phenyldichlorophosphate, DMSO and triethylamine ($Et_3N$) in isopropylacetate) or a Swern reaction (oxalyl chloride, DMSO and triethylamine ($Et_3N$) in methylene chloride). Another reagent that may be employed is the Jones reagent, a solution of chromic acid and sulfuric acid in $H_2O$.

Reaction Scheme L

As shown in Reaction Scheme L, the amine adducts may be formed by treatment of the enone 5 with the required amine in solvents such as methanol, ethanol, isopropanol, water and the like and mixtures thereof at ambient temperature. Other solvents, such as tetrahydofuran, ether and the like, may also be used in conjunction with the formerly mentioned hydroxylic solvents as mixtures. Other amines, in addition to the ethylamine described in the Examples and not restricted to primary amines, may also be used, such as benzylamine, methylamine, dimethylamine, propylamine and the like.

Reaction Scheme M

As shown in Reaction Scheme M the 14-hydroxy group of a macrolide may be eliminated by treatment with p-toluenesulfonic acid, benzenesulfonic acid or methanesulfonic acid in an inert organic solvent such as benzene, or toluene at from 40° C. to 60° C., for about 0.5 to 6 hours, or a sufficient period of time to eliminate the 14-hydroxy group. Neutralization with an aqueous solution of a weak base such as aqueous saturated sodium bicarbonate gives the 14,15-dehydro macrolides 23. The 14-hydroxy group may also be eliminated by activation followed by basic elimination, as described in U.S. Pat. No. 4,894,366.

In cases when there are no other competing olefins present, compound 23 may be reduced to the saturated analog 24 by utilizing any of the many methods of catalytic hydrogenation.

Reaction Scheme N

A hydroxyl or fluoro group may be introduced at C-20 essentially by the procedures of Reaction Scheme N. The suitably protected macrolide 28 is oxidized at C-20 by treatment with selenium dioxide in an alcoholic solvent such as ethanol in the presence of pyridine at solvent reflux temperature to give the 20-hydroxy macrolide (29). The 20-hydroxy macrolide may be further derivatized at C-20 by alkylation, acylation or phosphorylation to give ether, ester or phosphate derivatives by procedures well known to the practitioner of the art. As further illustrated, treatment of the 20-hydroxy macrolide 29 with diethylaminosulfur trifluoride in an inert organic solvent such as methylene chloride, chloroform or the like at a temperature of about 0° C. to –90° C., preferably about –78° C., gives the 20-fluoro 4", 14-di-OTBS macrolide (30). The procedures of Reaction Scheme J may be conducted prior to, concurrent with, or subsequent to the procedures of Reaction Schemes A–M.

Reaction Scheme O

Suitably modified and protected compound 31 may be modified in the tricarbonyl region. Keto group at the 2-position may be selectively reduced using several procedures. Reaction of compound 31 with sodium borohydride (NaBH$_4$) in isopropanol at reduced temperatures may provide compound 32. Alternatively, Samarium iodide (SmI$_2$) in THF and methanol at −78° C. with slow warming to rt is also effective.

C$_2$-hydroxy analog 32 may be converted to methylene derivative 33 a two-step sequence. The first step requires activation by use of methanesulfonyl anhydride, for example, to give the methanesulfonate ester. This may be carried out in pyridine. The second step requires reaction with a mercaptan reagent such as paramethoxybenzylmercaptan (PMB-SH) in a solvent such as DMF with Et$_3$N in an oxygenated atmosphere. This reaction sequence may be accomplished in good yield.

The procedures of Reaction Scheme O may be conducted prior to, concurrent with, or subsequent to the procedures of Reaction Schemes A–N.

Reaction Scheme P

The C-1 hydroxy group of compound 34 may be removed by dehydration using triphenylphosphine (Ph$_3$P) and diethylazodicarboxylate (DEAD) in THF at reduced temperatures to provide dehydro derivative 35.

Compound 35 may be selectively reduced to saturated analog 36 by conjugate reduction. One reagent that is particularly effective is potassium triphenylborohydride (KHBPh$_3$) in THF at −78° C.

The procedures of Reaction Scheme P may be conducted prior to, concurrent with, or subsequent to the procedures of Reaction Schemes A–N.

By suitable selection of protecting groups and the sequence of synthetic steps, all possible variations of substitution may be achieved.

The object compounds of Formula I obtained according to the reactions as explained above can be isolated and purified in a conventional manner, for example, extraction, precipitation, fractional crystallization, recrystallization, chromatography, and the like.

It is to be noted that in the aforementioned reactions and the post-treatment of the reaction mixture therein, the stereoisomer(s) of starting and object compounds due to asymmetric carbon atom(s) or double bond(s) of the object compounds of Formula I may occasionally be transformed into the other stereo isomer(s), and such cases are also included within the scope of the present invention.

In the present invention, compounds with asymmetric centers may occur as racemates, as diastereomeric mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (*J. Am. Chem. Soc.* 1989, 111, 1157; *J. Am. Chem. Soc.* 1990, 112, 2998; *J. Org. Chem.* 1990, 55, 2786; *J. Am. Chem. Soc.* 1990, 112, 5583. *Tetrahedron Lett.* 1988, 29, 277; *Tetrahedron Lett.* 1988, 29, 281; *Tetrahedron Lett.* 1988, 29, 3895; *J. Org. Chem.* 1988, 53, 4643; *Tetrahedron Lett.* 1988, 29, 4245; *Tetrahedron Lett.* 1988, 29, 4481; *J. Org. Chem.* 1989, 54, 9; *J. Org. Chem.* 1989, 54, 11; *J. Org. Chem.* 1989, 54, 12; *J. Org. Chem.* 1989, 54, 15; *J. Org. Chem.* 1989, 54, 17; *Tetrahedron Lett.* 1989, 30, 919; *Tetrahedron Lett.* 1989, 30, 1037; *J. Org. Chem.* 1989, 54, 2785; *J. Org. Chem.* 1989, 54, 4267; *Tetrahedron Lett.* 1989, 30, 5235; *Tetrahedron Lett.* 1989, 30, 6611; *Tetrahedron Lett.* 1989, 30, 6963; *Synlett* 1990, 38; *J. Org. Chem.* 1990, 55, 2284; *J. Org. Chem.* 1990, 55, 2771; *J. Org. Chem.* 1990, 55, 2776; *Tetrahedron Lett.* 1990, 31, 1439; *Tetrahedron Lett.* 1990, 31, 1443; *Tetrahedron Lett.* 1990, 31, 3007; *Tetrahedron Lett.* 1990, 31, 3283, 3287).

The compounds of the present invention are capable of forming salts with various inorganic and organic acids and bases and such salts are also within the scope of this invention. Examples of such acid addition salts (which are negative counterions defined herein as M$^-$) include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts (which are positive counterions defined herein as M$^+$) include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

C. Utility of the compounds within the scope of the invention

The compounds of Formula I may be employed as immunosuppressants or antimicrobial compounds by methods and in dosages known in the prior art for compounds of Formula II. These compounds possess pharmacological activity such as immunosuppressive activity, antimicrobial activity, and the like, and therefore are useful for the treatment and prevention of the resistance to transplantation or transplantation rejection of organs or tissues (such as heart, kidney, liver, lung, bone marrow, cornea, pancreas, intestinum tenue, limb, muscle, nervus, medulla ossium, duodenum, small-bowel, medulla ossium, skin, pancreatic islet-cell, etc. including xeno transplantation), graft-versus-host diseases by medulla ossium transplantation, autoimmune diseases such as rheumatoid arthritis, systemic lupus erythematosis, nephrotic syndrome lupus, Hashimoto's thyroiditis, multiple sclerosis, myasthenia gravis, type I diabetes mellitus, type II adult onset diabetes, uveitis, nephrotic syndrome, steroid-dependent and steroid-resistant nephrosis, Palmo-planter pustulosis, allergic encephalomyelitis, glomerulonephritis, etc., and infectious diseases caused by pathogenic microorganisms.

The compounds of Formula I are also useful for treating inflammatory, proliferative and hyperproliferative skin diseases and cutaneous manifestations of immunologically-mediated illnesses such as: psoriasis, psoriatic arthritis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, acne Alopecia areata, eosinophilic fasciitis, and atherosclerosis. More particularly, the compounds of Formula I are useful in hair revitalizing, such as in the treatment of male or female pattern alopecia or alopecia senilis, by providing epilation prevention, hair germination, and/or a promotion of hair generation and hair growth.

The compounds of Formula I are further useful in the treatment of respiratory diseases, for example sarcoidosis, fibroid lung, idiopathic interstitial pneumonia, and reversible obstructive airways disease, including conditions such as asthma, including bronchial asthma, allergic asthma, intrinsic asthma, extrinsic asthma and dust asthma, particularly chronic or inveterate asthma (for example late asthma and airway hyperreponsiveness), bronchitis and the like. The compounds of Formula I may also be useful for treating hepatic injury associated with ischemia.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. For example, the compounds of Formula I may be utilized with hydroxypropyl methylcellulose essentially as described in U.S. Pat. No. 4,916,138, issued Apr. 10, 1990, or with a surfactant essentially as described in EPO Publication 0,428,169. Oral dosage forms may be prepared essentially as described by T. Hondo, et al., *Transplantation Proceedings*, 1987, XIX, Supp. 6, 17–22. Dosage forms for external application may be prepared essentially as described in EPO Publication 0,423,714. The active object compound is included in the pharmaceutical composition in an amount sufficient to produce the desired effect upon the process or condition of diseases.

For the treatment of these conditions and diseases caused by immmunoirregularity a compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of reversible obstructive airways disease, it is preferable that the compound of Formula I be administered by inhalation to the lung, especially in the form of a powder.

For modifying the activity and/or toxicity of FK-506-type immunosuppressants, a compound of Formula I may be administered prior to, in conjuction with or subsequent to the administration of an FK-506-type of a compound.

The compounds of Formula I may optionally be employed in co-therapy with anti-proliferative agents. Particularly preferred is co-therapy with an antiproliferative agent selected from the group consisting of azathioprine (AZA), brequinar sodium, deoxyspergualin (DSG), mizaribine, mycophenolic acid morpholino ester (RS-61443), cyclosporin and rapamycin.

The compounds of Formula I may also be employed in conjunction with (or in a pharmaceutical composition additionally comprising):

(1) a 5α-reductase inhibitor, (2) a cyclosporin, (3) a potassium channel opener (such as minoxidil), or (4) a phospholipid.

Such co-therapy is particularly useful in hair revitalizing, such as in the treatment of male pattern alopecia, female pattern alopecia, alopecia senilis or alopecia areata, by providing epilation prevention, hair germination, and/or a promotion of hair generation and hair growth.

Such co-therapy is further useful in treating the hyperandrogenic conditions of androgenic alopecia, acne vulgaris, seborrhea, and female hirsutism.

For co-therapy of these conditions and diseases a compound of Formula I may be administered in combination with prior to, concurrent to, or subsequent to the administration of other agent(s).

For hair revitalizing the compound of Formula I may be administered topically or orally. Cyclosporin may be administered topically or orally. Although the 5α-reductase inhibitor or the potassium channel opener may be administered topically or orally, it is preferable that it be administered topically to the scalp. For unitary formulation, however, the preferred mode of administration is topically. It is especially preferred that the hair revitalizing composition of the present invention is administered by a percutaneous administration or by spraying onto the skin.

Dosage levels of the compounds of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 mg per patient per day, assuming a 70 kg patient). In addition, the compounds of the present invention may be administered on an intermittent basis; i.e. at daily, semiweekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally comprise from about 0.01 mg to about 500 mg, and preferably about 0.5 mg to about 100 mg of active ingredient. For external administration the compound of Formula I may be formulated within the range of, for example, 0.0001% to 60% by weight, preferably from 0.001 to 10% by weight, and most preferably from about 0.005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

PREPARATION OF STARTING INTERMEDIATES

EXAMPLE 1

17-Ethyl-1-hydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 500 mg of 17-ethyl-1,14-di-hydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in 7 ml of benzene was treated with 10 mg of p-toluenesulfonic acid and the solution was heated at 60° C. for two hours. The reaction mixture was quenched into saturated sodium bicarbonate solution and extracted with ethyl acetate. The combined organic layers were washed with water and saturated sodium chloride solution, dried with anhydrous magnesium sulfate and concentrated. The residue was chromatographed on silica gel (66% ethyl acetate: 33% hexane: 1% methanol) to give 350 mg of product. This material was dissolved in 10 ml of ethyl acetate and treated with 15 mg of 5% Rh/C. A balloon containing hydrogen was placed over the reaction mixture and the mixture stirred until the reaction was complete. The mixture was filtered through diatomaceous earth, concentrated and the residue subjected to chromatography (75% CH$_2$Cl$_2$:5% MeOH:20% Hexane) to give 294 mg of product.

EXAMPLE 2

17-Ethyl-1-hydroxy-12-[2'-(4",3"-dihydroxyoxycyclohexyl)-1'-methylvinyl]-23,25-dimethoxy-13,19,21,27-tetramethyl-11,28-dioxa-4-azatricyclo[22.3.10$^{4,9}$]octacos-18-ene-2,3,10,16-tetraone A solution of 17-ethyl-1,14-dihydroxy-12-[2'-(4"-hydroxy-3"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (210 mg) and a catalytic amount of p-toluenesulfonic acid in 40 ml of benzene was refluxed for 4 hours under a nitrogen atmosphere. The solvent was removed under reduced pressure and the dark residue was purified by chromatography (silica gel, 7% i-propanol/CH$_2$Cl$_2$) to give 17-ethyl-1-hydroxy-12-[2'-(4",3"-dihydroxycyclohexyl)-1'-methylvinyl]-23,25-dimethoxy-13,19,21,-27-tetramethyl-11,28-dioxa-4-azatricyclo-[22.3.1.0$^{4,9}$]octacos-14,18-diene-2,3,10,16-tetraone (180 mg) as a white solid. This material was dissolved in ethanol (20 ml) and treated with 5% Rh/C (40 mg).

Hydrogen was introduced via balloon for 30 min. and the mixture was filtered through celite. Removal of solvent followed by chromatography (silica gel) gave 172 mg of the title compound. Mass, $^1$H and 13C NMR data were consistent with the title structure.

EXAMPLE 3

17-Ethyl-1-hydroxy-12-[2'-(4"-hydroxy-3"-methoxycyclohexyl)-1'-methylvinyl]-14-triisopropyl-silyloxy-23,25-dimethoxy-13,19,21,27-tetramethyl-11,28-dioxa-4-azatricyclo[22.3.1.0$^{4,9}$]octacos-18-ene-2,3,10,16-tetraone

Step 3A

17-Ethyl-1-hydroxy-12-[2'-(4"-triisopropylsilyloxy-3"-methoxycyclohexyl)-1'-methylvinyl]-14-triisopropylsilyloxy-23,25-dimethoxy-13,19,21,27-tetramethyl-11,28-dioxa-4-azatricyclo[22.3.1.0$^{4,9}$]octacos-18-ene-2,3,10,16-tetraone To a cooled solution (0° C.) of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (120 mg) in dry methylene chloride (15 ml) was added 2,6-lutidine (64.3 mg) followed by triisopropylsilyl-trifluoromethane sulfonate (184 mg). Reaction temperature was raised to rt and stirred overnight under nitrogen atmosphere. The reaction was quenched with 10 ml of water and extracted with ethyl acetate. Organic layer was washed (water, sat'd NaHCO$_3$, sat'd NaCl) and dried (anhydrous MgSO$_4$). Removal of solvent followed by chromatography on silica gel (70% hexane/ethyl acetate) gave 150 mg of product. MASS: (FAB) 1110 (M$^+$+Li).

Step 3B

17-Ethyl-1-hydroxy-12-[2'-(4"-hydroxy-3"-methoxycyclohexyl)-1'-methylvinyl]-14triisopropylsilyloxy-23,25-dimethoxy-13,19,21,27-tetramethyl-11,28-dioxa-4-azatricyclo[22.3.1.0$^{4,}$ $_9$]octacos-18-ene-2,3,10,16-tetraone The title compound from the previous preparation (680 mg) was dissolved in methylene chloride (45 ml) and 10% solution of p-toluenesulfonic acid in methanol (45 ml) was added with stirring. The mixture was stirred at room temperature and the progress was followed by tlc analysis. After 4 hr, reaction was quenched with sat'd sodium bicarbonate and extracted with ethyl acetate three times. Normal work-up and removal of solvent followed by purification on silica gel column (80% ethyl acetate/hexane) gave 560 mg of the title compound as a white solid. MASS: (FAB) 954 (M$^+$+Li).

EXAMPLE 4

17-Ethyl-1-hydroxy-12-[2'-(4"-hydroxy-3"-methoxycyclohexyl)-1'-methylvinyl]-14t-butyldimethylsilyloxy-23,25-dimethoxy-13,19,21,27-tetramethyl-11,28-dioxa-4-azatricyclo[22.3.1.0$^{4,}$ $_9$]octacos-18-ene-2,3,10,16-tetraone

Step 4A

17-Ethyl-1-hydroxy-12-[2'-(4"-t-butyldimethylsilyloxy-3"-methoxycyclohexyl)-1'-methylvinyl]-14-t-butyldimethylsilyloxy-23,25-dimethoxy-13,19,21,27-tetramethyl-11,28-dioxa-4-azatricyclo[22.3.1.0$^{4,9}$]octacos-18-ene-2,3,10,16-tetraone To a cooled solution (0° C.) of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (395 mg) in dry methylene chloride (15 ml) was added 2,6-lutidine (160 mg) followed by t-butyldimethylsilyl triflouromethanesulfonate (250 mg). The reaction was stirred under nitrogen atmosphere and then the temperature was raised to rt. After 6 hr, the reaction was quenched with 10 ml of water and extracted with ethyl acetate. The organic layer was washed (water, saturated NaHCO$_3$, saturated NaCl) and dried (anhydrous MgSO$_4$). Removal of solvent under reduced pressure gave 500 mg of crude product. MASS: (FAB) 1023 (M$^+$+Li).

Step 4B

17-Ethyl-1-hydroxy-12-[2'-(4"-hydroxy-3"-methoxycyclohexyl)-1'-methylvinyl]-14-t-butyl-dimethylsilyloxy-23,25-dimethoxy-13,19,21,27-tetramethyl-11,28-dioxa-4-azatricyclo[22.3.1.0$^{4,9}$] octacos-18-ene-2,3,10,16-tetraone The product from Step 4A (500 mg) was dissolved in acetonitrile (20 ml) and 100 ml of hydrogen fluoride (48%)

was added. The reaction was stirred for 20 minutes at room temperature, quenched with saturated sodium bicarbonate, then extracted with ethyl acetate. Removal of solvent in vacuo followed by chromatography on silica gel (80% ethyl acetate/hexane) gave 300 mg of product (Mass, $^1$H and $^{13}$C NMR data consistent with the title compound.

EXAMPLE 5

17-Ethyl-1-hydroxy-12-[2'-(4"-(tert-butyldimethylsiloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (Example 2, 3.01 g) in dry methylene chloride (70 ml) was added an excess of imidazole (809 mg) followed by tert-butyldimethylsilyl chloride (716 mg). After 3 days of stirring at room temperature, the mixture was diluted with ethyl acetate which in turn was washed with 1N HCl, saturated sodium bicarbonate and brine, dried over magnesium sulfate and purified by flash chromatography (ethyl acetate:hexane (1:3)) to give the title compound (941 mg). $^1$H NMR consistent with the desired structure.

EXAMPLE 6

17-Ethyl-20-fluoro-1-hydroxy-12-[2'-(4"-(hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step 6A

17-Ethyl-1-hydroxy-12-[2'-(4"-(tert-butyldimethylsilyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos 18-ene-2,3,10,16-tetraone To a solution of 17-ethyl-1-hydroxy-12-[2'-(4"-hydroxy-3"-methoxycyclohexyl)-1'-methylvinyl]-23,25-dimethoxy-13,19,21,-27-tetramethyl-11,28-dioxa-4-azatricyclo[22.3.1.0$^{4,9}$]octacos-18-ene-2,3,10,16-tetraone (200 mg) in dry methylene chloride (3 ml) was added an excess of 2,6-lutidine (45 ml) and the mixture was stirred at room temperature. After 10 minutes, tert-butyldimethylsilyl trifluoromethanesulfonate (64 ml) was added by syringe. After 15 minutes the reaction mixture was diluted with ethyl acetate, extracted from saturated bicarbonate, washed with brine and the organic phase dried over magnesium sulfate. Removal of solvent in vacuo and flash chromatography on silica gel (ethyl acetate:hexane (1:2)+1% methanol) gave the title compound (235 mg). ($^1$H NMR consistent with the desired structure).

Step 6B

17-Ethyl-1,20-dihydroxy-12-[2'-(4"-tert-butyldimethylsilyloxy)-3"-methoxycyclohexyl)-4"1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1-hydroxy-12-[2'-(4"-(tert-butyldimethylsilyloxy)-3"-methoxycyclohexyl)-1'-methylvinyl]-23,25-dimethoxy-13,19,21,27-tetramethyl-11, 28-dioxa-4-azatricyclo[22.3.1.0$^{4,9}$]octacos-18-ene-2,3,10, 16-tetraone (235 mg) in 95% ethanol (2.2 ml) was added 53 ml of pyridine followed by selenium dioxide (58 mg). The flask was fitted with a water condenser and heated to 70° C. on a mantle. After 20 hours the mixture was cooled to room temperature filtered through diatomaceous earth and the filtrate poured into a saturated sodium bicarbonate solution. This was extracted with ethyl acetate, washed with brine and dried over magnesium sulfate. The solution was concentrated and purified by flash chromatography on silica gel (ethyl acetate:hexane (1:2)+1% methanol) to give the title compound (89 mg). ($^1$H NMR consistent with the desired structure).

Step 6C

17-Ethyl-20-fluoro-1-hydroxy-12-[2'-(4"-(tert-butyldimethylsiloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-20-dihydroxy-12-[2'-(4"-(tert-butyldimethylsiloxy)-3"-methoxycyclohexyl)-1'-methylvinyl]-23,25-dimethoxy-13,19,21,27-tetramethyl-11, 28-dioxa-4-azatricyclo[22.3.1.0$^{4,9}$]octacos-18-ene-2,3,10, 16-tetraone (30.5 mg) in methylene chloride (0.5 ml) was cooled to −78° C. in a dry ice/isopropanol bath. To this stirred solution, diethylaminosulfur trifluoride (4.5 ml) was added. After 3 minutes, saturated sodium bicarbonate (500 ml) was added followed by ethyl acetate (2 ml) and the mixture was warmed to room temperature. Extraction from ethyl acetate, drying over magnesium sulfate and purification by flash chromatography on silica gel (ethyl acetate:hexane (1:2)+1% MeOH) gave the title compound (22 mg). ($^1$H NMR consistent with the desired structure).

Step 6D

17-Ethyl-20-fluoro-1-hydroxy-12-[2'-(4"-(hydroxy-3"-methoxy-cyclo-hexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-20-fluoro-1-hydroxy-12-[2'-(4"-(tert-butyldimethylsiloxy)-3"-methoxycyclohexyl)-1'-methylvinyl]-23,25-dimethoxy-13,19,21,27-tetramethyl-11, 28-dioxa-4-azatricyclo[22.3.1.0$^{4,9}$]octacos-18-ene-2,3,10, 16-tetraone (7 mg) in acetonitrile (0.3 ml) was added a solution of 2% hydrogen fluoride in aqueous acetonitrile (100 ml), and the mixture stirred at room temperature. After 2 hours the solution was diluted with ethyl acetate, extracted with saturated sodium bicarbonate and the organic phase dried by passage through a magnesium sulfate column. Purification of the concentrate by flash chromatography on silica gel (ethyl acetate:hexane (1:1)+1% methanol) gave the title compound. MASS:(FAB) 816 (M+Na). Partial $^{13}$C NMR δ: 211.5 (C-16); 196.1 (2) 169.3(10); 165.0 (3); 138.1 (C-19); 135.8 (C-1'); 121.0 (C-18' major); 84.1 (C-3"); 43.1 (C-15); 26.0 (C-21).

EXAMPLE 7

17-Ethyl-1,20-dihydroxy-12-[2'-(4"-(hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,20-dihydroxy-12-[2'-(4"-(tert-butyldimethylsiloxy)-3"-methoxycyclohexyl)-1'- methylvinyl]-23,25-dimethoxy-13,19,21,27-tetramethyl-11, 28-dioxa-4-azatricyclo[22.3.1.0$^{4,9}$]octacos-18-ene-2,3,10, 16-tetraone (7 mg) (Step 6B) in acetonitrile (0.3 ml) was added a solution of 2% hydrogen fluoride in aqueous acetonitrile (100 ml), and the mixture stirred at room temperature. After 28 hours the solution was diluted with ethyl acetate, extracted with saturated sodium bicarbonate and the organic phase dried by passage through a magnesium sulfate column. Purification of the concentrate by flash chromatography on silica gel (ethyl acetate:hexane (2:1)+1% methanol) gave the title compound.

EXAMPLE 8

17-Ethyl-1,14,20-trihydroxy-12-[2'-(4"-hydroxy-3"-ethoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (5.15 gm, 0.065 mol) in glacial acetic acid (500 ml) at room temperature, was added a solution of selenium dioxide (9.27 gm, 0.083 mol) in H$_2$O (90 ml). The reaction mixture was stirred at room temperature for 41 hours whereupon, it was poured into a stirred mixture of H$_2$O (3 L) and celite. After stirring for 15 minutes, the mixture was filtered through a pad of celite and extracted with diethyl ether (1×2 L, 2×1 L). The organic fractions were washed with saturated sodium bicarbonate and brine, dried over magnesium sulfate, filtrated and evaporated in vacuo. The product was purified by chromatography (silica, acetone:hexanes 2:5) to give the title compound MASS and $^1$H NMR were consistent with the structure.

EXAMPLE 9

17-Ethyl-1-hydroxy-12-[2'-(4"-oxo-3"-methoxycyclohexyl)-1'-methylvinyl]-14-t-butyldimethylsilyloxy-23,25-dimethoxy-13,19,21,27-tetramethyl-11,28-dioxa-4-azatricyclo[22.3.10$^{4,9}$] octacos 18-ene-2,3,10,16-tetraone A solution of 17-Ethyl-1-hydroxy-12-[2'-(4"-hydroxy-3"methoxycyclohexyl)-1'-methylvinyl]-14-t-butyldimethylsilyloxy-23,25-dimethoxy-13,19,21,27-tetramethyl-11,28-dioxa-4-azatricyclo-[22.3.1.0$^{4,9}$]octacos-18-ene-2,3,10,16-tetraone (Example 4) (30 gm, 0.0331 mol) in acetone (200 ml) was cooled to 0° C. To the solution was added 16.5 mL of Jones reagent (prepared by dissolving 26.72 g CrO$_3$ in 23 mL of concentrated H$_2$SO$_4$, then diluting the solution to 100 mL with H$_2$O) (The reaction was monitored by TLC 20% acetone/hexanes). After 60 minutes, the reaction was complete and excess oxidant was destroyed by slow addition of 10 mL of 2-propanol. After 10 min., the mixture had become bright green, and the reaction mixture was diluted with 800 mL of water and 1 L of ether. The layers were separated and the aqueous layer was washed with four equal portions of ether. Each ether layer was sequentially washed with two equal portions of water, then twice with 1M KHCO$_3$ solution, then with brine (Virtually all of the green color was removed following the KHCO$_3$ washes). MS: 796 (M+7). The ether layers were combined, dried over MgSO$_4$, and concentrated to a pale yellow gum that was lyophilized from benzene to afford 26.8 g (89%) of the title compound as a white solid. MS 796 (M+7).

EXAMPLE 10

17-Ethyl-1-hydroxy-14-tert-butyldimethylsilyl-12-[2'-(4"-oxo-3"-methoxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone To a solution of 17-ethyl-1-hydroxy-14-tert-butyldimethylsilyl-12-[2'-(4"-hydroxy-3"-methoxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (2 g) in isopropylacetate (9 ml) was added dimethylsulphoxide (0.63 ml) and the mixture cooled to −20° C. Triethylamine (1.54 ml) was added followed by phenyldichlorophosphate (0.66 ml) and the reaction warmed to 0° C. The reaction mixture was then poured into brine, extracted with ethyl acetate, dried (MgSO$_4$) and concentrated. The crude material was purified by column chromatography on silica gel eluting with 80% hexane:20% acetone to give the title compound as a white solid (1.75 g).

partial $^1$H NMR d: 5.50 (s, 1H minor); 5.22 (m, 3H major); 5.18 (d, J=11 Hz, 1H minor); 4.99 (d, J=11 Hz, 1H minor); 4.94 (d, J=6 Hz, 1H major); 4.78 (d, J=11 Hz, 1H major).

EXAMPLE 11

17-Ethyl-1-hydroxy-14-tert-butyldimethylsilyl-12-[2'-(4"-tert-butyldimethylsilyloxy-3"-methoxycyclohex-4"-enyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone To a solution of 17-ethyl-1-hydroxy-14-tert-butyldimethylsilyl-12-[2'-(4"-oxo-3"-methoxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (1.75 g) in dichloromethane (26.5 ml) was added triethylamine (0.81 ml) followed by tert-butyldimethylsilyltrifluoromethanesulphonate (1.34 ml) dropwise and the mixture stirred at room temperature for 40 minutes. The reaction mixture was then poured into saturated sodium bicarbonate solution, extracted with ethyl acetate, dried (MgSO$_4$) and concentrated. The crude mixture was purified by column chromatography on silica gel eluting with 90% hexane:10% acetone to give the title compound (1.56 g) as a white solid.

partial $^1$H NMR d: 5.50 (s, 1H minor); 5.35 (d, J=11 Hz, 1H major); 5.20 (s, 1H major); 5.18 (d, J=11 Hz, 1H major), 5.12 (d, J=11 Hz, 1H minor); 5.06 (d, J=11 Hz, 1H minor) 4.95 (d, J=6 Hz, 1H major); 4.88 (m, 1H); 4.79 (d, J=11 Hz, 1H major).

PREPARATION OF INSTANT COMPOUNDS

EXAMPLE 12

17-Ethyl-1,14-dihydroxy-12-[2'-(4"-oxo-3"-methoxycyclohex-5"-enyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (A) and 17-Ethyl-1,14-dihydroxy-12-[2'-(4"-oxo-3"-methoxycyclohex-2"-enyl)-1'-methylvinyl]-23,25-dimethoxy-13,19,21,27-tetramethyl-11,28-dioxa-4-azatricylclo[22.3.1.0$^{4,9}$] octacos-18-ene-2,3,10,16-tetraone (B)

To a solution of 17-ethyl-1-hydroxy-14-tert-butyldimethyisilyl-12-[2'-(4"-oxo-3"-methoxycyclohexyl)-

1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (94 mg) in THF (0.88 ml) at −78° C. under nitrogen was lithium hexamethyldisilazide (416 ml). The reaction was stirred at −78° C. for 30 minutes before the addition of phenylselenyl chloride (666 ml of a solution of 60 mg of PhSeCl in 1 ml THF). After stirring for a further 20 minutes the reaction was then quenched by pouring into saturated sodium bicarbonate solution. This was extracted with ethyl acetate, dried (MgSO$_4$), concentrated and purified by column chromatography on silica gel to give 17-ethyl-1-hydroxy-14-tert-butyldimethylsilyl-12-[2'-(4"-oxo-3"-methoxy-5"-(selenophenyl)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone and 17-ethyl-1-hydroxy-14-tert-butyldimethylsilyl-12-[2'-(4"-oxo-3"-methoxy-3"-(selenophenyl)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (68 mg) as a mixture.

This mixture was then dissolved in THF (3 ml) at 0° C. and treated with acetic acid (3.3 ml) followed by 30% aqueous hydrogen peroxide solution (15 ml). The reaction was allowed to warm to room temperature where it was poured into saturated sodium bicarbonate solution and extracted with ethyl acetate, dried (MgSO$_4$) and concentrated. Purification by column chromatography on silica gel eluting with 70% hexane:30% acetone% gave 17-ethyl-1-hydroxy-14-tert-butyldimethylsilyl-12-[2'-(4"-oxo-3"-methoxycyclohex-5"-enyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (A) eluting first, as a white solid (5.8 mg) and 17-ethyl-1-hydroxy-14-tert-butyldimethylsilyl-12-[2'-(4"-oxo-3"-methoxycyclohex-2"-enyl)-1'-methylvinyl]-23,25-dimethoxy-13,19,21,27-tetramethyl-11,28-dioxa-4-azatricylclo [22.3.1.0$^{4,9}$]octacos-18-ene-2,3,10,16-tetraone (B) eluting second, as a white solid (24 mg). The compounds above were each deprotected in a manner similar to that described above to give the title compounds as white solids.

MS(FAB): Compound A 811 (M$^+$+Na); Compound B 795 (M$^+$+Li).

partial $^1$H NMR Compound A d: 6.54 (dt, J=8, 2 Hz, 1H); 5.96 (dt, J=9.7, 3.5 Hz, 1H); 5.36 (s, 1H major); 5.23 (s, 1H minor); 5.10 (t, J=5 Hz, 2H). Compound B d: 5.52 (d, J=4 Hz, 1H minor); 5.51 (d, J=4 Hz, 1H major); 5.35 (s, 1H major); 5.24 (s, 1H minor); 5.19 (t, J=9 Hz, 2H); 4.89 (s, 1H minor); 4.60 (d, J=5 Hz, 1H).

EXAMPLE 13

17-Ethyl-1-hydroxy-14-tert-butyldimethylsilyl-12-[2'-(3"-methoxy-4"-oxo-5"-hydroxycyclohexyl)-1'-methylvinyl]-23,25-dimethoxy-13,19,21,27-tetramethyl-11,28-dioxa-4-azatricylclo[22.3.1.0$^{4,9}$] octacos-18-ene-2,3,10,16-tetraone To a solution of 17-ethyl-1-hydroxy-14-tert-butyldimethylsilyl-12-[2'-(4"-tert-butyldimethylsilyloxy-3"-methoxycyclohex-4"-enyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (1 g) in an acetone (11.6 ml)-water (1.78 ml) mixture at 0° C. was added N-methylmorpholine-N-oxide (127 mg) followed by a solution of osmium tetroxide in t-butanol (0.25 ml of a solution of 20 mg OsO$_4$ in 1 ml t-BuOH). The reaction was allowed to stir for 4 hours before being diluted with ethyl acetate and washed with 20% sodium bisulphite and saturated sodium bicarbonate solution. After being dried (MgSO$_4$) and concentrated the crude material was dissolved in dichloromethane (10 ml) and treated with 1% p-toluene sulphonic acid in methanol (1 ml). The reaction was stirred at room temperature for 45 minutes before being washed with saturated sodium bicarbonate, dried (MgSO$_4$) and concentrated. The crude mixture was purified by column chromatography on silica gel eluting with 70% hexane:30% acetone to give the title compound as a white solid (442 mg).

partial $^1$H NMR d: 5.53 (d, J=9 Hz, 1H major); 5.50 (s, 1H minor); 5.39 (d, J=9Hz, 1 H minor); 5.22 (m, 3H major); 5.08 (d, J=9 Hz, 1H minor); 4.98 (d, J=3 Hz, 1H major); 4.79 (d, J=9 Hz, 1H major).

EXAMPLE 14

17-Ethyl-1,14-dihydroxy-12-[2'-(3"-methoxy-4",5"-dihydroxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone To a solution of 17-ethyl-1-hydroxy-14-tert-butyldimethylsilyl-12-[2'-(3"-methoxy-4"-oxo-5"-hydroxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (35 mg) in 1:1 acetic acid/acetone (0.5 ml) at −15° C. was added a solution of sodium triacetoxyborohydride in acetic acid (0.1 ml; prepared by adding an excess of sodium borohydride to acetic acid). The reaction was quenched by careful addition of saturated sodium bicarbonate solution and extraction with ethyl acetate. The crude material was purified by column chromatography on silica gel eluting with 70% hexane:30% acetone to give 17-ethyl-1-hydroxy-14-tert-butyldimethylsilyl-12-[2'-(3"-methoxy-4",5"-dihydroxycyclohexyl)-1'-methylvinyl]-23,25-dimethoxy-13,19,21,27-tetramethyl-11,28-dioxa-4-azatricylclo [22.3.1.0$^{4,9}$]octacos-18-ene-2,3,10,16-tetraone (18 mg) as a white solid.

A portion (14 mg) of this material was dissolved in THF (200 ml) at room temperature, treated with hydrogen fluoride in pyridine (8 drops) and stirred for 24 hours. The reaction was then quenched with saturated sodium bicarbonate solution, extracted with ethyl acetate, dried (MgSO$_4$) and concentrated. Further purification by column chromatography on silica gel eluting with 60% hexane:40% acetone gave the title compound (10 mg) as a white solid.

MS(FAB) 815(M$^+$+Li)

partial $^1$H NMR d: 5.32 (s, 1H major); 5.17 (m, 2H major); 4.99 (m, 2H); 4.86 (s, 1H minor); 4.58 (d, J=5 Hz, 1H major); 4.40(d, J-14 Hz, 1H major); 4.21 (s, 1H major).

EXAMPLE 15

17-Ethyl-1,14-dihydroxy-12-[2'-(3"-methoxy-4"-hydroxy-5"-(indol-5'"-yloxy)cyclohexyl)-1'-methylvinyl]-23,25-dimethoxy-13,19,21,27-tetramethyl-11,28-dioxa-4-azatricylclo[22.3.1.0$^{4,9}$] octacos-18-ene-2,3,10,16-tetraone To a solution of tri(indol-5-yl)bismuthine (29 mg) in dichloromethane (0.5 ml) was added peracetic acid (17 ml) in one portion and the mixture stirred until no bismuthine remained. Then 17-ethyl-1-hydroxy-14-tert-butyldimethylsilyl-12-[2'-(3"-methoxy-4",5"-dihydroxycyclohexyl)-1'-methylvinyl]-23,25-dimethoxy- 13,19,21,27-tetramethyl-11,28-dioxa-4-azatriclyclo[22.3.1.0$^{4,9}$]octacos-18-ene-2,3,10,16tetraone (15 mg) and copper acetate (11 mg) were added and the mixture heated to 40° C. for 2 hours. The reaction was then diluted with dichloromethane and washed with saturated bicarbonate solution. After further extraction with ethyl acetate the organic extracts were combined, dried (MgSO$_4$) and concentrated. Purification by column chromatography on silica gel eluting with 70% hexane:30% acetone yielded 17-ethyl-1-hydroxy-14-tert-butyldimethylsilyl-12-[2'-(3"-methoxy-4"-hydroxy-5"-(indol-5'"-yloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (5 mg) as a white solid. Deprotection of this compound in a manner similar to that described above gave the title compound as a white solid.

MS(FAB) 937 (M$^+$)

partial $^1$H NMR d: 7.18 (m, 2H); 7.01 (m, 1H); 6.92 (dd, J=3,9 Hz, 1H); 6.35 (m, 1H), 5.35 (s, 1H major); 5.22 (m, 2H major); 5.00 (m, 2H minor); 4.90 (s, 1H minor).

EXAMPLE 16

17-Ethyl-1,14-dihydroxy-12-[2'-(3"-methoxy-4"-hydroxy-5"-(m-methoxyphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described above using tri(m-methoxyphenyl)bismuthine as the arylating agent to give the title compound (7 mg) as a white solid.

MS(FAB) 920 (M$^+$+Li-1)

partial $^1$H NMR d: 7.13 (m 1H); 6.52 (m, 3H); 5.33 (s, 1H major); 5.19 (m, 2H, major); 5.00 (m, 2H major); 4.89 (s, 1H, minor).

EXAMPLE 17

17-Ethyl-1,14-dihydroxy-12-[2'-(3"-methoxy-4"-hydroxy-5"-(p-biphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described above using tri(p-biphenyl)bismuthine as the arylating agent to give the title compound as a white solid.

MS(FAB) 967 (M$^+$+Li)

partial $^1$H NMR 7.50 (dd, J=12,7 Hz, 4H); 7.39 (t, J=7 Hz, 2H); 7.28 (m, 1H); 7.04 (d, J=7 Hz, 2H); 5.33 (s, 1H).

EXAMPLE 18

17-Ethyl-1,14-dihydroxy-12-[2'-(3"-methoxy-4"-hydroxy-5"-(p-hydroxyphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described above using tri(p-hydroxyphenyl)-bismuthine as the arylating to give the title compound as a white solid.

MS(FAB) 906 (M$^+$+Li)

partial $^1$H NMR d: 6.84 (d, J=8Hz, 2H); 6.70 (d, J=8Hz, 2H); 5.32 (s, 1H).

EXAMPLE 19

17-Ethyl-1,14-dihydroxy-12-[2'-(3"-methoxy-4"-hydroxy-5"-(p-tolyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described above using tri(p-tolyl) bismuthine as the arylating agent to give the title compound as a white solid.

MS(FAB) 904 (M$^+$+Li)

partial $^1$H NMR d: 7.03 (d, J=7 Hz, 2H); 6.87 (d, J=7 Hz, 2H); 5.33 (s, 1H).

EXAMPLE 20

17-Ethyl-1,14-dihydroxy-12-[2'-(3"-methoxy-4"-hydroxy-5"-(p-hydroxyethylphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described above using tri(p-hydroxyethyl)bismuthine as the arylating agent to give the title compound as a white solid.

MS(FAB) 935 (M$^+$+Li)

partial $^1$H NMR d: 7.11 (d, J=7.5 Hz, 2H); 6.92 (d, J=7.5 Hz, 2H); 5.33 (s, 1H).

EXAMPLE 21

17-Ethyl-1,14-dihydroxy-12-[2'-(3"-methoxy-4"-hydroxy-5"-(o-fluorophenyloxy)cyclohexyl)-1'-methylvinyl]-23,25-dimethoxy-13,19,21,27-tetramethyl-11,28-dioxa-4azatricyclo[22.3.1.0$^{4,9}$]octacos-18-ene-2,3,10,16-tetraone Prepared essentially as described above using tri(p-fluoro)bismuthine as the arylating agent to give the title compound as a white solid.

MS(FAB) 909 (M$^+$+Li)

partial $^1$H NMR d: 7.11 (m, 1H); 7.02 (m, 2H); 6.92 (m, 1H); 5.33 (s, 1H).

EXAMPLE 22

17-Ethyl-1-hydroxy-14-tert-butyldimethylsilyl-12-[2'-(3"-methoxy-4"-acetoxy-5"-(indol-5'"-yloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-tert-butyldimethylsilyl-12-[2'-(3"-methoxy-4"-hydroxy-5"-(indol-5'"-yloxy)cyclohexyl)-1'-methylvinyl]-23,25-dimethoxy-13,19,21,27-tetramethyl-11,28-dioxa-4-azatricyclo[22.3.1.0$^{4,9}$]octacos-8-ene-2,3,10,16-tetraone (29 mg) in dichloromethane (2 ml) at 0° C. was added triethylamine (10 ml), acetic anhydride (5 ml) and 4-dimethylaminopyridine (catalytic amount) in that order and the reaction mixture allowed to stir for 45 minutes. The reaction mixture was diluted with dichloromethane, washed with brine, dried (MgSO$_4$) and concentrated. Purification by column chromatography on silica gel eluting with 70% hexane:30% acetone gave the title compound as a white solid (22 mg).

partial $^1$H NMR d: 7.30 (m, 1H); 7.18 (m, 1H); 6.98 (m, 2H); 6.37 (m, 1H); 5.47 (s, 1H minor); 5.30 (m, 2H major); 5.23 (d, J=3 Hz, 1H major); 5.21 (d, J=9 Hz, 1H major); 5.08 (t, J=9 Hz, 1H minor); 4.98 (d, J=4 Hz, 1H major); 4.80 (d, J=1 Hz, 1 h major); 4.59 (t, J=4 Hz, 1 h major); 4.55 (t, J=4 Hz, 1H minor).

EXAMPLE 23

17-Ethyl-1,14-dihydroxy-12-[2'-(3"-methoxy-4",5"-bisallyloxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (A), 17-Ethyl-1,14-dihydroxy-12-[2'-(3"-methoxy-4"-hydroxy-5"-allyloxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (B) and 17-Ethyl-1,14-dihydroxy-12-[2'-(3"-methoxy-4"-allyloxy-5"-hydroxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (C)

To a solution of the diol (30 mg) in cyclohexane (0.5 ml) and dichloromethane (0.25 ml) was added allyl-2,2,2-trichloroacetimidate (7 ml) followed by triflic acid (1 ml) and the reaction allowed to stir at room temperature for 3.5 hours. The reaction was quenched by pouring into saturated aqueous sodium bicarbonate solution and extracting with ethyl acetate. The organic extracts were dried (MgSO$_4$), concentrated and purified by column chromatography on silica gel eluting with 80% hexane:20% acetone to give 17-ethyl-1-hydroxy-14-tert-butyldimethylsilyl-12-[2'-(3"-methoxy-4",5"-bisallyloxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (A) (8.2 mg) and 17-ethyl-1-hydroxy-14-tert-butyldimethylsilyl-12-[2'-(3"-methoxy-4"-hydroxy-5"-allyloxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (B) and 17-ethyl-1-hydroxy-14-tert-butyldimethylsilyl-12-[2'-(3"-methoxy-4"-allyloxy-5"-hydroxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (C) as a mixture of regioisomers (17.2 mg). Deprotection of these compounds in a similar manner to that described above yielded the title compounds, (A) (6.5 mg) and (B and C) (8 mg), as white solids.

MS(FAB) Compound A 894 (M$^+$+Li) Compound B 855 (M$^+$+Li)

partial $^1$H NMR Compound A d: 5.88 (m, 2H); 5.26–4.90 (m, 7H); 4.55 (d, J=5 Hz, 1H). Compound B d: 5.88 (m, 1H); 5.32–4.85 (m, 7H); 4.55 (d, J=5 Hz, 1H).

EXAMPLE 24

17-Ethyl-1,14-dihydroxy-12-[2'-(3"-methoxy-4",5"-bisbenzyloxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (A) and 17-Ethyl-1,14-dihydroxy-12-[2'-(3"-methoxy-4"-hydroxy-5"-benzyloxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (B) and 17-Ethyl-1,14-dihydroxy-12-[2'-(3"-methoxy-4"-benzyloxy-5"-hydroxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (C)

Prepared essentially as described above using benzyl-2,2,2-trichloroacetimidate as reagent to give compound (A) and a regioisomeric mixture of (B) and (C) as white solids.

MS(FAB) Compound A 994 (M$^+$+Li) Compound B 904 (M$^+$+Li)

partial $^1$H NMR Compound A d: 7.28 (m, 10H); 5.42 (s, 1H major); 5.17 (s, 1H minor); 5.02 (m, 2H); 4.9 (s, 1H minor); 4.7 (d, J=13 Hz, 2H), 4.50 (m, 4H); 4.39 (d, J=13 Hz, 2H); 4.18 (s, 1H major). Compound B d: 7.30 (m, 5H); 5.32 (s, 1H major); 5.17 (s, 1H minor); 5.00 (m, 2H); 4.57 (d, J=13 Hz, 1H);, 4.45 (d, J=13 Hz, 1H); 4.20 (s, 1H major).

EXAMPLE 25

17-Ethyl-1-hydroxy-14-tri-isopropylsilyl-12-[2'-(3",4"-bisoxocyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone To a solution of 17-ethyl-1-hydroxy-14-triisopropylsilyl-12-[2'-(3",4"-dihydroxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (100 mg) in dichloromethane (0.5 ml) was added DMSO (23 ml) and the solution cooled to −78° C. Trifluoroacetic anhydride (44 ml) was then added and the solution stirred for 30 minutes before the addition of triethylamine (98 ml). The reaction was then warmed to room temperature and poured into brine, extracted with dichloromethane, dried (MgSO$_4$) and concentrated. The crude material was purified by column chromatography on silica gel eluting with 70% hexane:30% acetone to give the title compound (57 mg) as a white solid (57 mg).

partial $^1$H NMR d: 6.19 (dd, J=6,4 Hz, 1H major); 6.04 (dd, J=6,4 Hz, 1H minor); 5.95 (s, 1H minor); 5.90 (s, 1H major).

EXAMPLE 26

17-Ethyl-1-hydroxy-12-[2'-(3",4"-bisoxocyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone Prepared essentially as described above using 17-ethyl-1-hydroxy-12-[2'-(3",4"-dihydroxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (200 mg) as starting material to give the title compound (97 mg) as a white solid.

MS(FAB) 765 (M+Li)

partial $^1$H NMR d : 6.06 (m, 1H); 5.90 (m, 1H).

EXAMPLE 27

17-Ethyl-1,14-dihydroxy-12-[2'-(3"-methoxy-4",5"-bisoxocyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone Prepared essentially as described above using 17-ethyl-1-hydroxy-14tert-butyldimethylsilyl-12-[2'-(3"-methoxy-4"-oxo-5"-hydroxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (1.02 g) as starting material to give 17-ethyl-1-hydroxy-14-tert-butyldimethylsilyl-12-[2'-(3"-methoxy-4",5"-bisoxocyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (736 mg).

MS(FAB) 916 (M+Li)

EXAMPLE 28

17-Ethyl-1,14-dihydroxy-12-[2'-(4"-oxo-3"-methoxycyclohex-5"-enyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone A solution of 17-ethyl-1-hydroxy-14-tert-butyldimethylsilyl-12-[2'-(4"-tert-butyldimethylsilyloxy-3"-methoxycyclohex-4"-enyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (50 mg) in acetonitrile (0.5 ml) was added to a suspension of palladium (II) acetate (5 mg) and benzoquinone (3 mg) and the reaction stirred at ambient temperature for 3 days. The reaction mixture was then filtered through a pad of silica gel and celite rinsing with ethyl acetate. Purification by column chromatography on silica gel eluting with 80% hexane:20% acetone gave 17-ethyl-1-hydroxy-14-tert-butyldimethylsilyl-12-[2'-(4"-oxo-3"-methoxycyclohex-5"-enyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (10 mg) which was deprotected in the manner described above to give the title compound.

MS(FAB) 811 (M$^+$+Na)

partial $^1$H NMR δ: 6.54 (dt, J=8, 2 Hz, 1H); 5.96 (dt, J=9.7, 3.5 Hz, 1H); 5.36 (s, 1H major); 5.23 (s, 1H minor); 5.10 (t, J=5 Hz, 2H).

EXAMPLE 29

17-Ethyl-1,14-dihydroxy-12-[2'-(3"-methoxy-4"-oxo-6"-ethylaminocyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone To a solution of 17-ethyl-1-hydroxy-14-tert-butyldimethylsilyl-12-[2'-(3"-methoxy-4"-oxo-cyclohex-5"-enyl)-1'-methylvinyl]-23,25-dimethoxy-13,19,21,27-tetramethyl-11,28-dioxa-4azatricylclo[22.3.1.0$^{4,9}$]octacos-18-ene-2,3,10,16-tetraone (10 mg) in methanol (250 μl) was added ethylamine and the reaction stirred at ambient temperature for 30 minutes. The reaction mixture was then concentrated and purified by column chromatography on silica gel eluting with 65% haxane:35% acetone to give 17-ethyl-1-hydroxy-14-tert-butyldimethylsilyl-12-[2'-(3"-methoxy-4"-oxo-6"-ethylaminocyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (7.2 mg). This was deprotected in a manner similar to that described above to give the title compound as a white solid.

MS(FAB) 832 (M$^+$), 839 (M+Li).

EXAMPLE 30
T-Cell Proliferation Assay
1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at 2.5×10$^5$ cells/ml in complete culture medium composed of RPMI 1640 medium with 10% heat-inactivated fetal calf serum, 100 mM glutamine, 1 mM sodium pyruvate, 2×10$^{-5}$M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The various dilutions of the compound to be tested were then added in triplicate wells at 20 μl/well. The compound 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone was used as a standard. The culture plates were then incubated at 37° C. in a humidified atmosphere of 5% CO$_2$-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Betacounter). Mean counts per minute of replicate wells were calculated and the results expressed as concentration of compound required to inhibit tritiated thymidine uptake of T-cells by 50%.

A selection of compounds were tested according to the previous procedure. The title compounds of the following Examples had activity in inhibiting the proliferation of T-cells in the aforementioned assay:

12, 14, 15, 16, 17, 18, 19, 20, 21, 23, 24, 25, 26, 28, and 29.

The results of this assay are representative of the intrinsic immunosuppressive activity of the compounds of the present invention.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present phanraceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound which is selected from the group consisting of:

17-ethyl-1,14-dihydroxy-12-[2'-(4"-oxo-3"-methoxycyclohex-5"-enyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#1)

17-ethyl-1,14-dihydroxy-12-[2'-(4"-oxo-3"-methoxycyclohex-2"-enyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#2)

17-ethyl-1,14-dihydroxy-12-[2'-(3"-methoxy-4",5"-dihydroxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#3)

17-ethyl-1,14-dihydroxy-12-[2'-(3"-methoxy-4"-hydroxy-5"-(indol-5'"-yloxy)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#4)

17-ethyl-1,14-dihydroxy-12-[2'-(3"-methoxy-4"-hydroxy-5"-(m-methoxyphenyloxy)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#5)

17-ethyl-1,14-dihydroxy-12-[2'-(3"-methoxy-4"-hydroxy-5"-(p-biphenyloxy)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#6)

17-ethyl-1,14-dihydroxy-12-[2'-(3"-methoxy-4"-hydroxy-5"-(p-hydroxyphenyloxy)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#7)

17-ethyl-1,14-dihydroxy-12-[2'-(3"-methoxy-4"-hydroxy-5"-(p-tolyloxy)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#8)

17-ethyl-1,14-dihydroxy-12-[2'-(3"-methoxy-4"-hydroxy-5"-(p-hydroxyethylphenyloxy)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#9)

17-ethyl-1,14-dihydroxy-12-[2'-(3"-methoxy-4"-hydroxy-5"-(o-fluorophenyloxy)cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#10)

17-ethyl-1,14-dihydroxy-12-[2'-(3"-methoxy-4",5"-bisallyloxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#11)

17-ethyl-1,14-dihydroxy-12-[2'-(3"-methoxy-4"-hydroxy-5"-allyloxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#12)

17-ethyl-1,14-dihydroxy-12-[2'-(3"-methoxy-4"-allyloxy-5"-hydroxycyclohexyl)-1'-methylvinyl]-23,25-dimethoxy-13,19,21,27-tetramethyl-1,28-dioxa-4-azatricylclo[22.3.1.0$^{4,9}$]octacos-18-ene-2,3,10,16-tetraone; (#13)

17-ethyl-11,14-dihydroxy-12-[2'-(3"-methoxy-4",5"-bisbenzyloxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#14)

17-ethyl-1,14-dihydroxy-12-[2'-(3"-methoxy-4"-hydroxy-5"-benzyloxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#15)

17-ethyl-1,14-dihydroxy-12-[2'-(3"-methoxy-4"-benzyloxy-5"-hydroxycyclohexyl)-1'-methylvinyl]-23,25-dimethoxy-13,19,21,27-tetramethyl-11,28-dioxa-4-azatricylclo-[22.3.1.0$^{4,9}$]octacos-18-ene-2,3,10,16-tetraone; (#16)

17-ethyl-1-hydroxy-12-[2'-(3",4"-bisoxocyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#17)

17-ethyl-1,14-dihydroxy-12-[2'-(3"-methoxy-4",5"-bisoxocyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#18)

17-ethyl-1,14-dihydroxy-12-[2'-(4"-oxo-3"-methoxycyclohex-5"-enyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#19)

17-ethyl-1,14-dihydroxy-12-[2'-(3"-methoxy-4"-oxo-6"-ethylaminocyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone; (#20)

or a pharmaceutically acceptable salt thereof.

* * * * *